United States Patent
Shimokawa et al.

(10) Patent No.: US 10,539,493 B2
(45) Date of Patent: Jan. 21, 2020

(54) PARTICULATE MATTER DETECTION SENSOR AND PARTICULATE MATTER DETECTION APPARATUS

(71) Applicant: DENSO CORPORATION, Kariya, Aichi-pref. (JP)

(72) Inventors: Hironobu Shimokawa, Nishio (JP); Kazuhiko Koike, Nishio (JP); Masahiro Yamamoto, Kariya (JP); Go Miyagawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 252 days.

(21) Appl. No.: 15/657,503

(22) Filed: Jul. 24, 2017

(65) Prior Publication Data

US 2018/0024038 A1    Jan. 25, 2018

(30) Foreign Application Priority Data

Jul. 25, 2016 (JP) .................................. 2016-145841
Jan. 19, 2017 (JP) ................................. 2017-007545

(51) Int. Cl.
*G01N 15/06* (2006.01)
*G01M 15/10* (2006.01)
*G01N 15/00* (2006.01)

(52) U.S. Cl.
CPC ...... *G01N 15/0656* (2013.01); *G01M 15/102* (2013.01); *G01N 15/0606* (2013.01); *G01N 2015/0046* (2013.01)

(58) Field of Classification Search
CPC .......... G01N 15/0606; G01N 15/0656; G01N 2015/0046; G01M 15/10; G01M 15/102
USPC ........ 73/23.31, 28.01, 31.05, 114.69, 114.71
See application file for complete search history.

(56) References Cited

U.S. PATENT DOCUMENTS

| | | |
|---|---|---|
| 4,656,832 A | 4/1987 | Yukihisa et al. |
| 7,543,477 B2 | 6/2009 | Berger et al. |
| 2006/0151338 A1* | 7/2006 | Wang ................. G01N 27/4071 205/780.5 |
| 2007/0119233 A1 | 5/2007 | Schnell et al. |
| 2007/0158191 A1 | 7/2007 | Berger |
| 2008/0000286 A1 | 1/2008 | Strohmaier et al. |
| 2009/0126458 A1 | 5/2009 | Fleischer et al. |
| 2010/0192671 A1* | 8/2010 | Losing .................. G01F 1/6983 73/23.31 |
| 2011/0030451 A1 | 2/2011 | Roesch et al. |

(Continued)

FOREIGN PATENT DOCUMENTS

| | | |
|---|---|---|
| DE | 10 2006 040 351 A1 | 3/2008 |
| JP | 2016-138449 | 8/2016 |
| WO | 2008/031654 A1 | 3/2008 |

OTHER PUBLICATIONS

"Resistivity Test Methods"—https://www.gotopac.com/art-esd-resistivity.*

*Primary Examiner* — Benjamin R Schmitt
(74) *Attorney, Agent, or Firm* — Nixon & Vanderhye P.C.

(57) ABSTRACT

The particulate matter detection sensor includes a conductive part, and the pair of electrodes that are arranged at specified spacing so as to face each other. The conductive part is formed into a plate shape using a conductive material having electrical resistivity that is higher than particulate matter. One major surface of the conductive part functions as an accumulation surface on which particulate matter accumulates. The pair of electrodes are formed on this accumulation surface.

10 Claims, 24 Drawing Sheets

(56) References Cited

U.S. PATENT DOCUMENTS

2012/0103059 A1\* 5/2012 Kimata .................. F01N 11/00
 73/23.33
2013/0283886 A1 10/2013 Teranishi et al.

\* cited by examiner

FIG.7
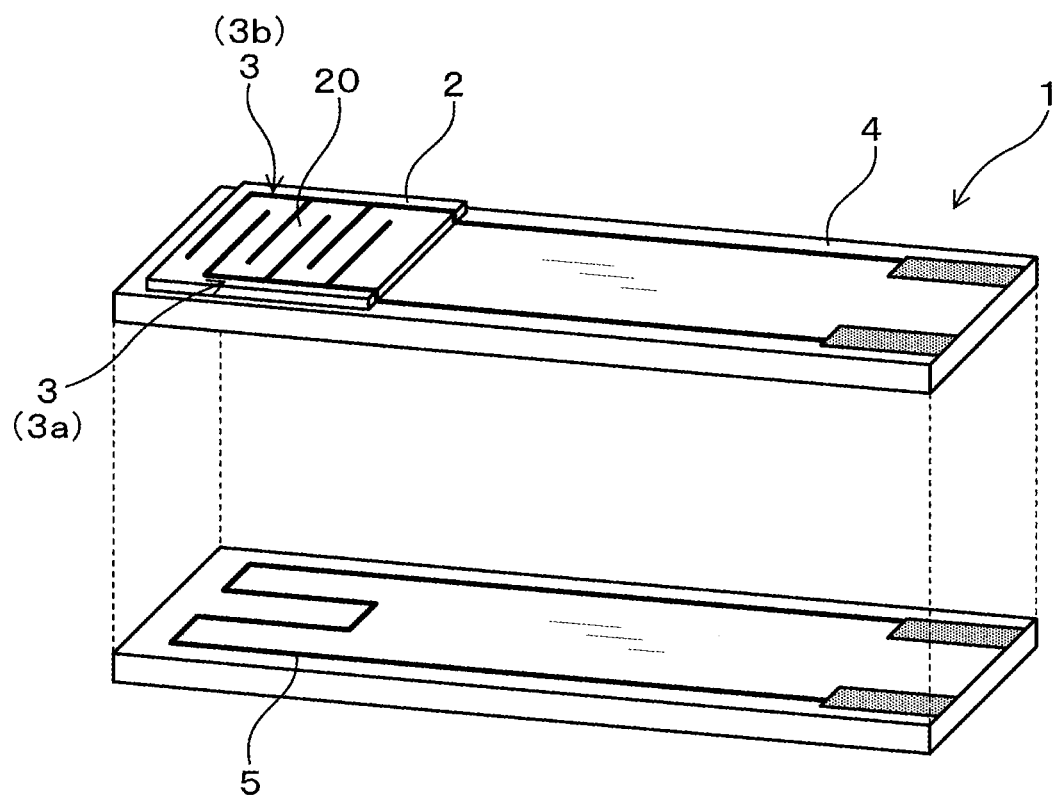
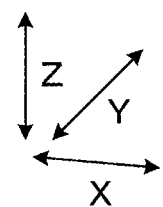

PARTICULATE MATTER DETECTION SENSOR AND PARTICULATE MATTER DETECTION APPARATUS

CROSS-REFERENCE TO RELATED APPLICATION

This application is based on and claims the benefit of priority from earlier Japanese Patent Applications No. 2016-145841 filed on Jul. 25, 2016 and No. 2017-7545 filed on Jan. 19, 2017, the description of which is incorporated herein by reference.

TECHNICAL FIELD

The present disclosure relates to a particulate matter detection sensor for detecting an amount of particulate matter included in exhaust gases, and a particulate matter detection apparatus that uses the particulate matter detection sensor.

BACKGROUND

As a particulate matter detection sensor (hereafter, also referred to as "PM sensor") for detecting an amount of particulate matter included in exhaust gases, a sensor is known that includes an insulating substrate made of ceramics or the like, and a pair of electrodes that are arranged on the insulating substrate so as to face each other with a predetermined space therebetween. The particulate matter is formed of soot or the like that has electrical conductivity. Therefore, when particulate matter accumulates between the pair of electrodes, an electrical current flows between the pair of electrodes via the particulate matter. The PM sensor is configured such that the amount of the electrical current is measured, whereby the amount of the particulate matter included in the exhaust gases is calculated.

However, in the PM sensor described above, in the case where only a small amount of the particulate matter accumulates between the pair of electrodes, because an electrical current path is not formed between the electrodes using the particulate matter, the electrical current does not flow (refer to FIG. 27). In this PM sensor, the electrical current starts to flow after a large amount of the particulate matter accumulates between the pair of electrodes and then the electrical current path is formed between the electrodes using the particulate matter (refer to FIG. 28). Therefore, the PM sensor described above has a problem in that when only a small amount of the particulate matter is accumulated, the electrical current does not flow between the electrodes and it is not possible to detect the particulate matter. That is, there is a problem in that the detection sensitivity for detecting the particulate matter is low.

In order to solve this problem, a PM sensor has been invented in which a pair of electrodes are covered by a conductive part having an electrical resistivity that is higher than the particulate matter (refer to U.S. Pat. No. 7,543,477 as Patent Document 1). In this PM sensor, when the particulate matter accumulates on the surface of the conductive part, the electrical current flows from one electrode to the surface of the conductive surface and passes through the particulate matter having lower resistivity toward the other electrode (refer to FIG. 31). Therefore, even when the amount of accumulated particulate matter is comparatively small, the current flowing between the electrodes changes, so it is considered possible to detect that the particulate matter is accumulated.

However, in Patent Document 1, there is room for improving detection precision of the PM sensor for detecting the particulate matter. In other words, the PM sensor described above is such that electrodes are covered by the conductive part, so when the particulate matter accumulates on the surface of the conductive part (refer to FIG. 31) and then the electrical current flows through the particulate matter, the electrical current passes through a portion from one of the electrodes to the surface of the conductive part. A portion disposed from one of the electrodes to the conductive part is defined as "portion A". Therefore, when there is variation of the thickness of the portion A during the manufacturing, an electrical resistance varies, and thus a current between the electrodes varies. As a result, it is not possible to measure accurately an amount of the particulate matter. Accordingly, a PM sensor is desired to be able to further improve the detection accuracy for detecting particulate matter.

SUMMARY

The present embodiment provides a particulate matter detection sensor that is able to increase a detection sensitivity and improve a detection accuracy for detecting particulate matter, and to provide a particulate matter detection apparatus that uses that particulate matter detection sensor.

A first aspect of the present disclosure is the particulate matter detection sensor for detecting an amount of particulate matter that is included in exhaust gases, and includes:

a conductive part that is formed into a plate shape using a conductive material having electrical resistivity that is higher than the particulate matter, with one major surface functioning as the accumulation surface on which the particulate matter accumulates; and a pair of electrodes that are formed on the accumulation surface and are arranged so as to be separated from each other and so as to face each other.

Moreover, a second aspect of the present disclosure is the particulate matter detection apparatus, and includes:

a particulate matter detection sensor, and a control unit that is electrically connected to the particulate matter detection sensor; wherein the control unit includes:

a voltage-applying unit that applies a voltage between the pair of electrodes;

a electrical-current-measurement unit that measures electrical current that flows between the pair of electrodes; and a calculation unit that calculates the amount of particulate matter that is included in exhaust gases based on a measurement value of the electrical current.

The particulate matter detection sensor includes a conductive part that is formed into the plate shape using the conductive material having the electrical resistivity that is higher than the particulate matter. The one major surface of the conductive part is made for the accumulation surface on which the particulate matter accumulates. The above-described pair of electrodes are formed on the accumulation surface.

Therefore, it is possible to improve the detection sensitivity for detecting particulate matter. In other words, in the particulate matter detection sensor, a pair of electrodes is formed on a surface (an accumulation surface) of the conductive part, so when voltage is applied between the electrodes in a state in which there is absolutely no particulate matter accumulated, electrical current can flow in the accumulation surface without flowing inside the conductive part. Accordingly, even when there is only a small amount of particulate matter accumulated on the accumulation surface, electrical current is able to flow in the particulate matter having lower electrical resistance than the conductive part, and thus it is possible to increase the electrical current between the electrodes. Consequently, even when there is only a small amount of particulate matter accumulated, it is possible to detect the particulate matter, and it becomes possible to increase the detection sensitivity for detecting particulate matter.

Moreover, in the particulate matter detection sensor described above, the pair of electrodes is formed on a major surface of the conductive part, or in other words, on the accumulation surface, so electrical current flows in the accumulation surface in an arrangement direction of the electrodes (refer to FIG. 3), and electrical current mostly does not flow in the thickness direction of the conductive part. Therefore, variation in the thickness of the conductive part is unlikely to affect the detection. Hence, it is possible to increase the detection accuracy for detecting particulate matter.

Furthermore, the particulate matter detection apparatus includes the particulate matter detection sensor. Therefore, it is possible to increase the detection sensitivity and improve the detection accuracy for detecting particulate matter that is included in exhaust gases.

In the aspects described above, it is possible to provide a particulate matter detection sensor and particulate matter detection apparatus that uses the particulate matter detection sensor capable of increasing the detection sensitivity and improving the detection accuracy for detecting particulate matter.

The "major surface" described above means a surface having the largest surface area in the surfaces of the conductive part.

BRIEF DESCRIPTION OF THE DRAWINGS

In the drawings:

FIG. 7 is an exploded perspective view of particulate matter detection sensor of the first embodiment;

DETAILED DESCRIPTION OF THE PREFERRED EMBODIMENTS

The particulate matter detection sensor described above can be a vehicle particulate matter detection sensor for installation in an automobile.

(First Embodiment)

Figure 1:
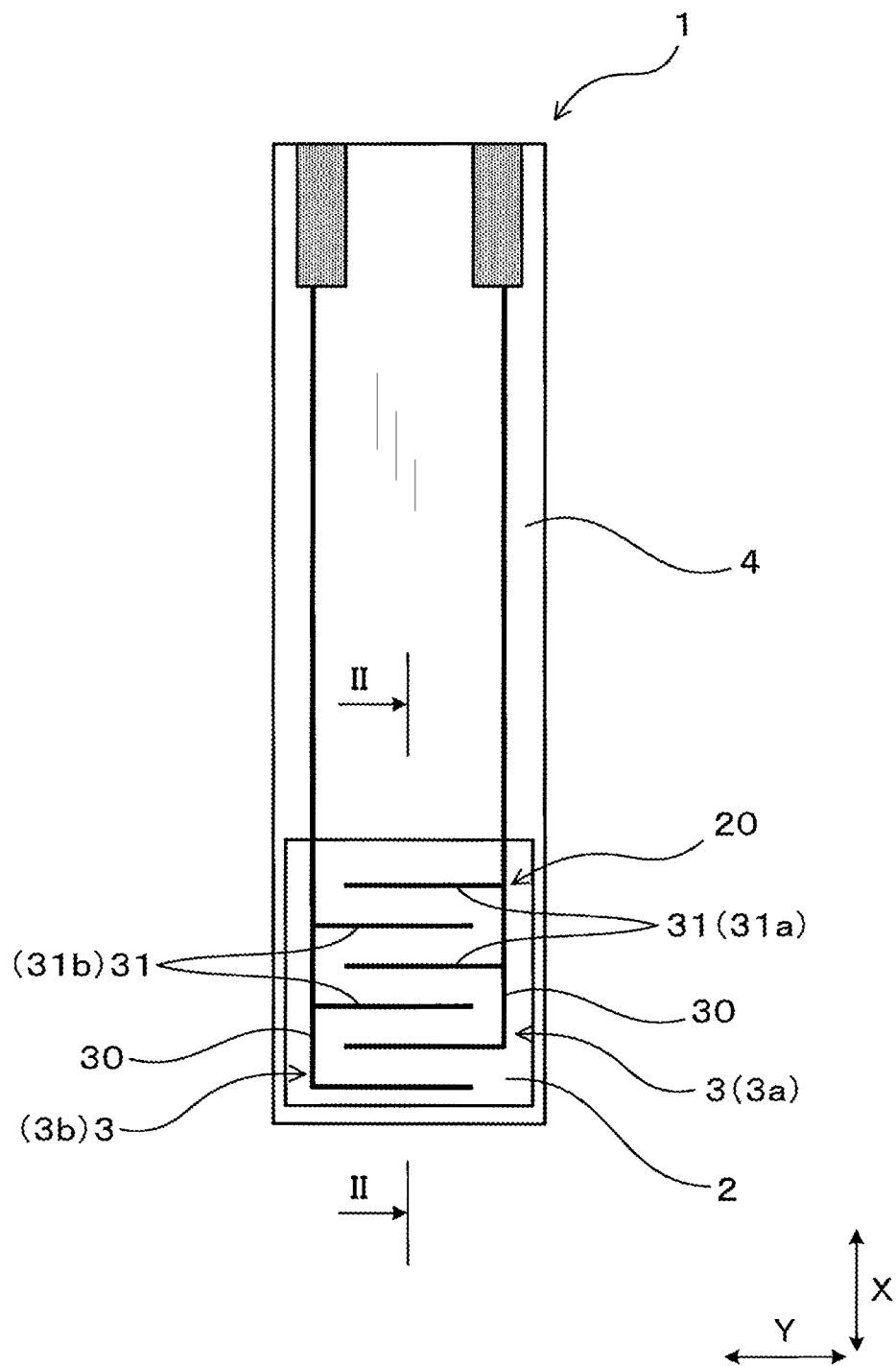
FIG. 1 is a plan view of a particulate matter detection sensor of a first embodiment, and is a view seen from an arrow direction I in FIG. 2.

An embodiment of the particulate matter detection sensor (hereinafter, also referred to as "PM sensor") and particulate matter detection apparatus described above will be explained with reference to FIG. 1 to FIG. 9. A PM sensor 1 of the present embodiment is used for detecting an amount of particulate matter 6 (refer to FIG. 4 and FIG. 5) that is included in exhaust gases. As illustrated in FIG. 1 and FIG. 7, the PM sensor 1 of the present embodiment includes a conductive part 2 and a pair of electrodes 3 (3a, 3b).

Figure 2:
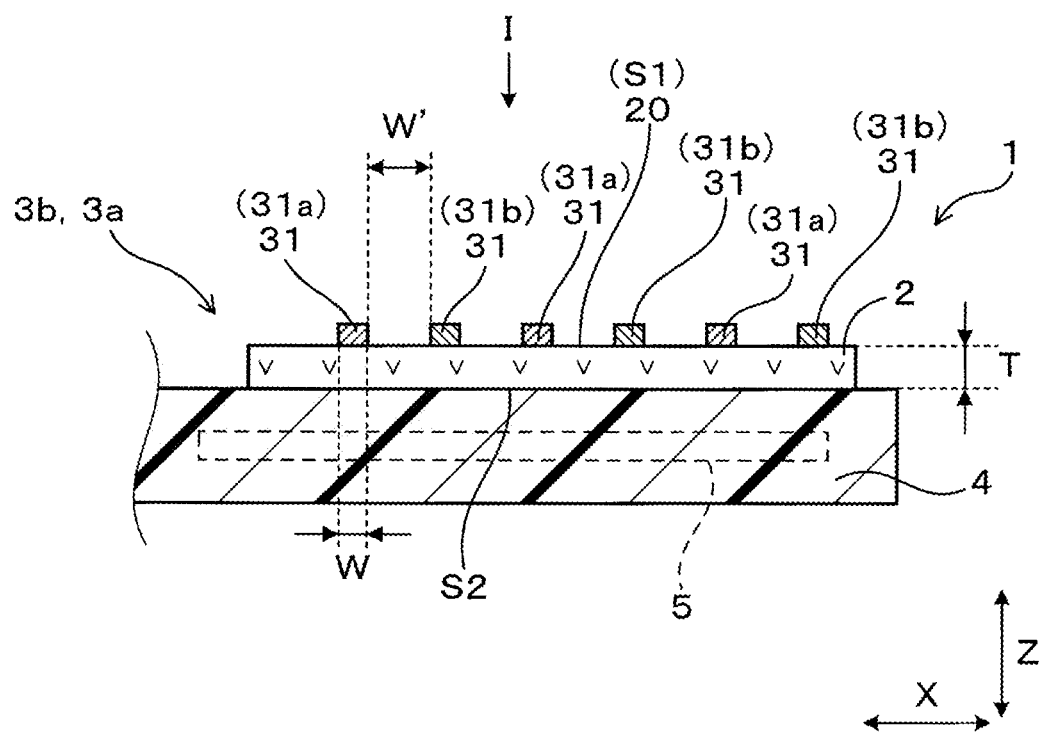
FIG. 2 is a sectional view of section II-II in FIG. 1.

The conductive part 2 is formed into a plate shape using a conductive material having a higher electrical resistivity than the particulate matter 6. As illustrated in FIG. 2, one major surface S1 of the conductive part 2 is set to be an accumulation surface 20 where the particulate matter 6 accumulates. Another major surface S2 of the conductive part 2 is contacted with a substrate section 4 that is made of an insulating material.

The pair of electrodes (3a, 3b) is formed on an accumulation surface 20. These electrodes 3a, 3b are arranged so as to be separated from each other and to face each other.

Figure 9:
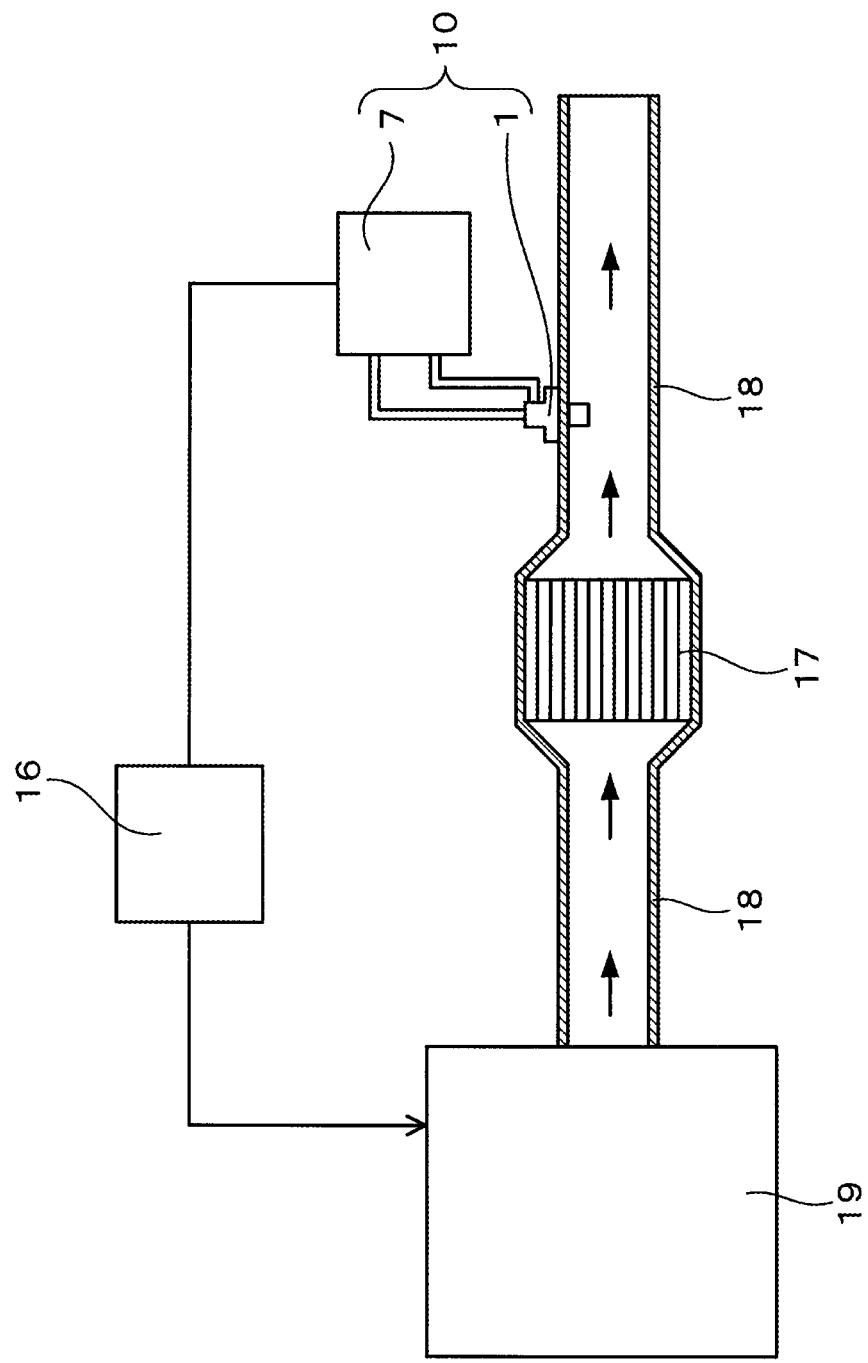
FIG. 9 is a diagram illustrating the installation position of a particulate matter detection sensor of the first embodiment.

The PM sensor 1 of the present embodiment is a vehicle PM sensor that is to be installed in the automobile. As illustrated in FIG. 9, an automobile includes an engine 19 and an exhaust pipe 18 that is connected to the engine 19. A cleaning apparatus 17 for removing particulate matter 6 that is in the exhaust gases is provided in the exhaust pipe 18. An apparatus in which the cleaning apparatus 17 and the exhaust pipe 18 are integrated is defined as an apparatus A.

The apparatus A has both ends so as to face each other. An upstream end of the apparatus A in a direction in which gas flows is defined as a first end, and a downstream end is defined as a second end. The PM sensor 1 is installed between the second end and the cleaning apparatus 17. In the present embodiment, the amount of particulate matter 6 that is included in the exhaust gases having passed through the cleaning apparatus 17 is detected using the PM sensor 1. Then, fault diagnosis of the cleaning apparatus 17 is performed using this detection value.

The engine 19 of the present embodiment is a diesel engine that is equipped with a supercharger, however, the engine is not limited to a diesel engine. The cleaning apparatus 17 of the present embodiment is an oxidation catalyst (DOC) and diesel particulate filter (DPF). However, even in a gasoline engine, there is a need to suppress the emission of particulate matter, so in order to satisfy this need, it is also possible to arrange a PM sensor 1 between the second end and a cleaning apparatus for a gasoline engine which is a so-called three-way catalyst or particulate filter (GPF). Particularly, it is possible to improve detection accuracy for detecting particulate matter using the PM sensor 1 of the present embodiment in a direct injection type gasoline engine, so it is possible to perform suitable feedback control of the engine, and it is possible to improve precision of injection control.

Moreover, as described above, the PM sensor 1 of the present embodiment includes a substrate 4 that is made of an insulating material (ceramics). As illustrated in FIG. 2 and FIG. 7, a heater 5 is provided in the substrate 4. Configuration is such that when a large amount of the particulate matter 6 is accumulated on the accumulation surface 20, the particulate matter 6 is burned using the heater 5 and is removed.

As illustrated in FIG. 1, electrodes 3a, 3b include common sections 30, and comb-tooth sections 31 that extend from the common sections 30. The comb-tooth sections 31a that are formed on one of the electrodes 3a, and the comb-tooth sections 31b that are formed on the other electrode 3b are arranged in an alternating manner. As illustrated in FIG. 2, a width W of a comb-tooth section 31 in an arrangement direction (X direction) of the comb-tooth sections 31 is shorter than a space W' between the comb-tooth sections 31.

The conductive material of the conductive part 2 may include a metal oxide having conductivity. As the conductive material, it is possible to use ceramics having perovskite structure, for example. When a molecular formula of the ceramics is set to be $ABO_3$, A is preferably at least one element selected from among La, Sr, Ca, and Mg, and B is preferably one element selected from among Ti, Al, Zr and Y.

The conductive material of the conductive part 2 is a material that has a larger electrical resistivity than the particulate matter, and has slight conductivity.

The electrical resistivity of the particulate matter can be measured by a powder resistance measurement method below. In other words, a cylindrical container (cross-sectional area A), in which powder is placed, having a bottom surface and a top surface made of electrode plates, and in this state, a distance L between the electrodes and a resistance value R between the electrodes are measured while applying a pressure to the electrode plate on the top surface of the cylindrical container, and compressing the powder (PM) in a vertical axis direction of the cylindrical container. With this measurement method, the resistivity $\rho$ of the powder (PM) is calculated from $R \times (A/L)$.

In the present embodiment, the resistance R is measured using a cylindrical container having a 6 mm diameter $\phi$ cross-section (cross-sectional area of $2.83 \times 10^{-5}$ $m^2$), and in a state of applying a pressure of 60 kgf.

As a result of the measurement using this method, the resistivity of the PM was $10^{-3}$ to $10^2$ $\Omega \cdot cm$. This is because, depending on an engine state, an electrical resistivity of the generated PM changes. For example, PM that is discharged from an engine that is operating under high load and at high speed has little unburned hydrocarbon component content, and mostly is made up of soot, so the resistivity of the PM is about $10^{-3}$ $\Omega \cdot cm$. Moreover, the PM that is discharged from an engine that is operating at a low rotational rate and a small load includes a large amount of unburned hydrocarbon component, so the resistivity of the PM is high, and is about $10^2$ $\Omega \cdot cm$. Therefore, preferably the electrical resistivity of the conductive part 2 of the present embodiment is at least $10^2$ $\Omega \cdot cm$ or more.

Figure 3:
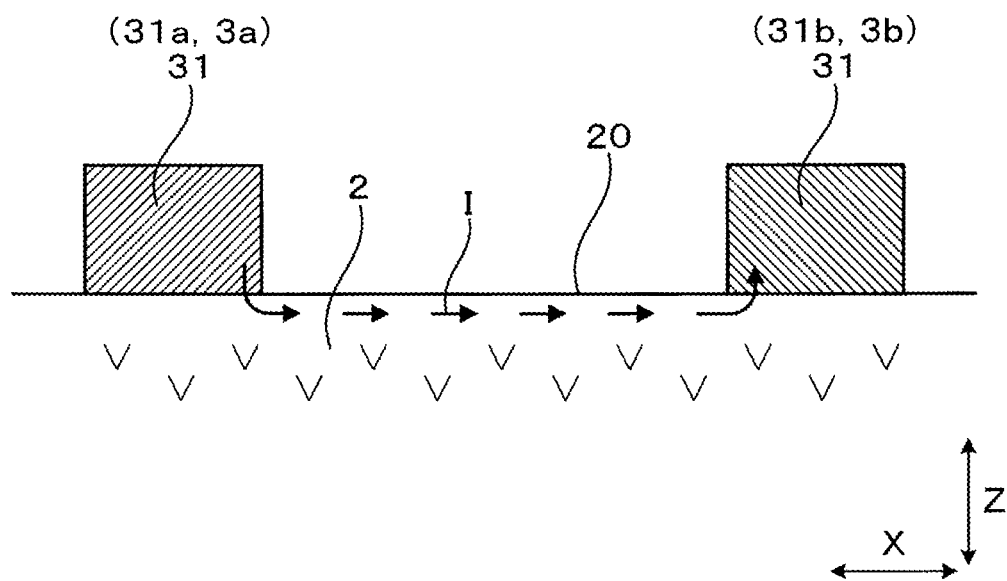
FIG. 3 is an enlarged cross-sectional view of the particulate matter detection sensor of the first embodiment in a state in which no particulate matter is accumulated.

The conductive part 2 has electrical conductivity, as illustrated in FIG. 3, therefore even when there is absolutely no particulate matter 6 accumulated on the accumulation surface 20, an electrical current I flows between the pair of electrodes 3a, 3b.

Figure 4:
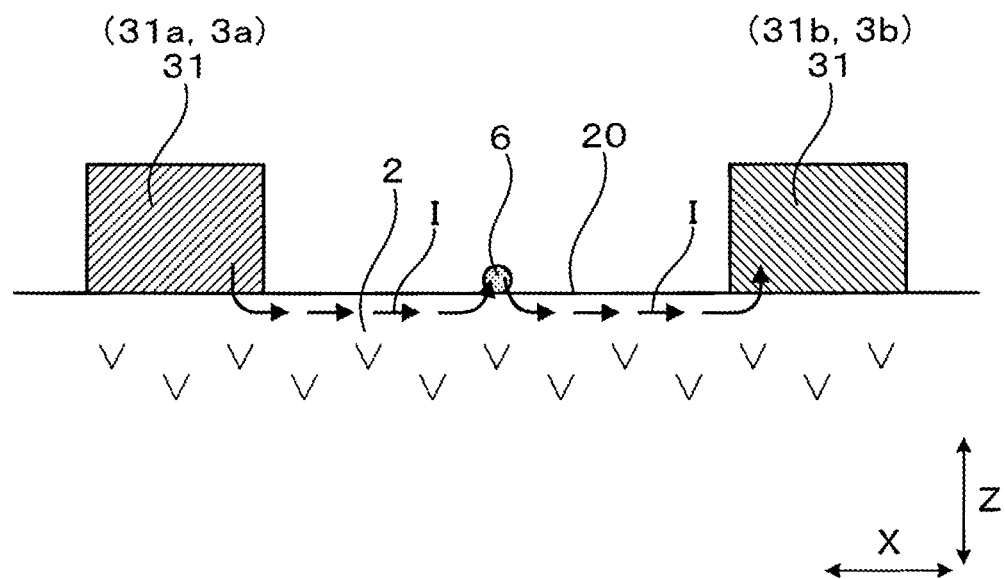
FIG. 4 is an enlarged cross-sectional view of the particulate matter detection sensor of the first embodiment in a state in which a little particulate matter is accumulated.
Figure 5:
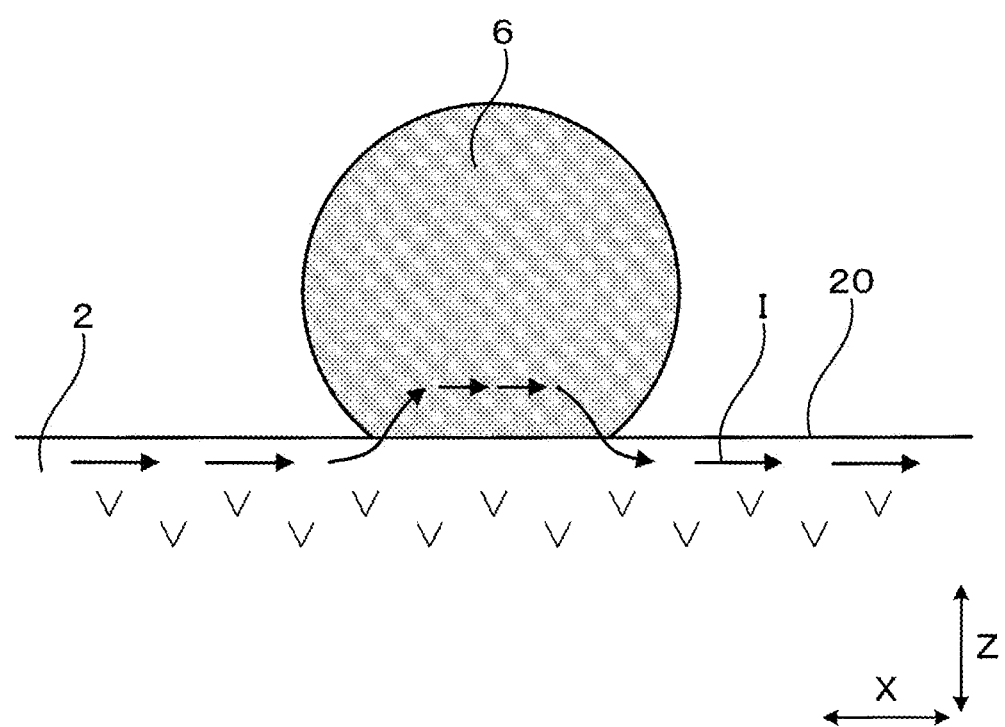
FIG. 5 is an enlarged view of a main part of FIG. 4.
Figure 6:
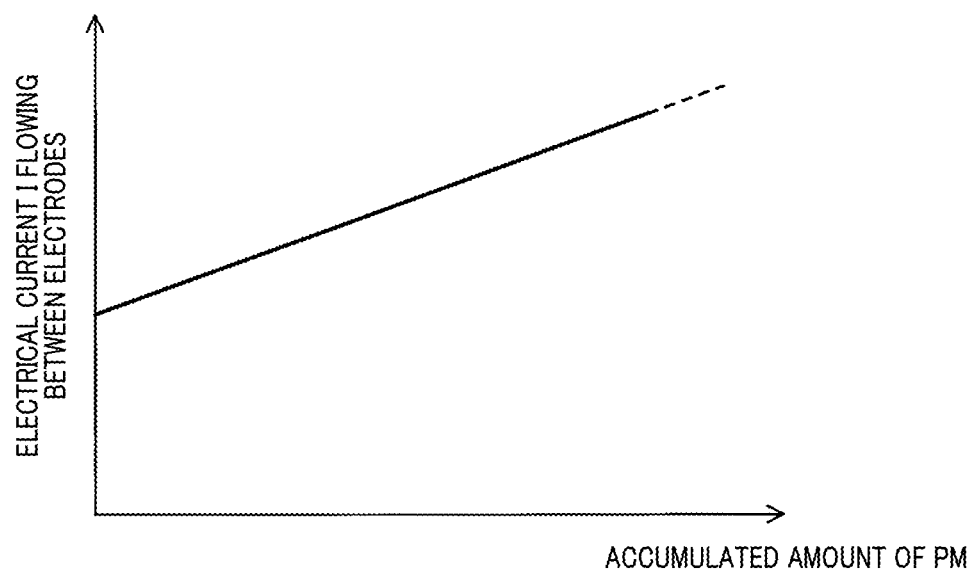
FIG. 6 is a graph illustrating the relationship between an accumulated amount of particulate matter and a current flowing between electrodes in the first embodiment.

Moreover, as illustrated in FIG. 4 and FIG. 5, when the particulate matter 6 is accumulated on the accumulation surface 20, the current I flows through the particulate matter 6 having a resistivity that is lower than the conductive part 2. Therefore, as illustrated in a graph in FIG. 6, as an amount of the accumulated particulate matter 6 increases, the current I that flows between the electrodes 3a, 3b increases. Consequently, by storing the graph shown in FIG. 6 beforehand, it is possible to calculate the amount of the particulate matter 6 that is accumulated on the accumulation surface 20. Furthermore, using this calculated amount and the time that was required for particulate matter 6 to accumulate, it is possible to calculate the amount of the particulate matter 6 that is included in exhaust gases.

Figure 8:
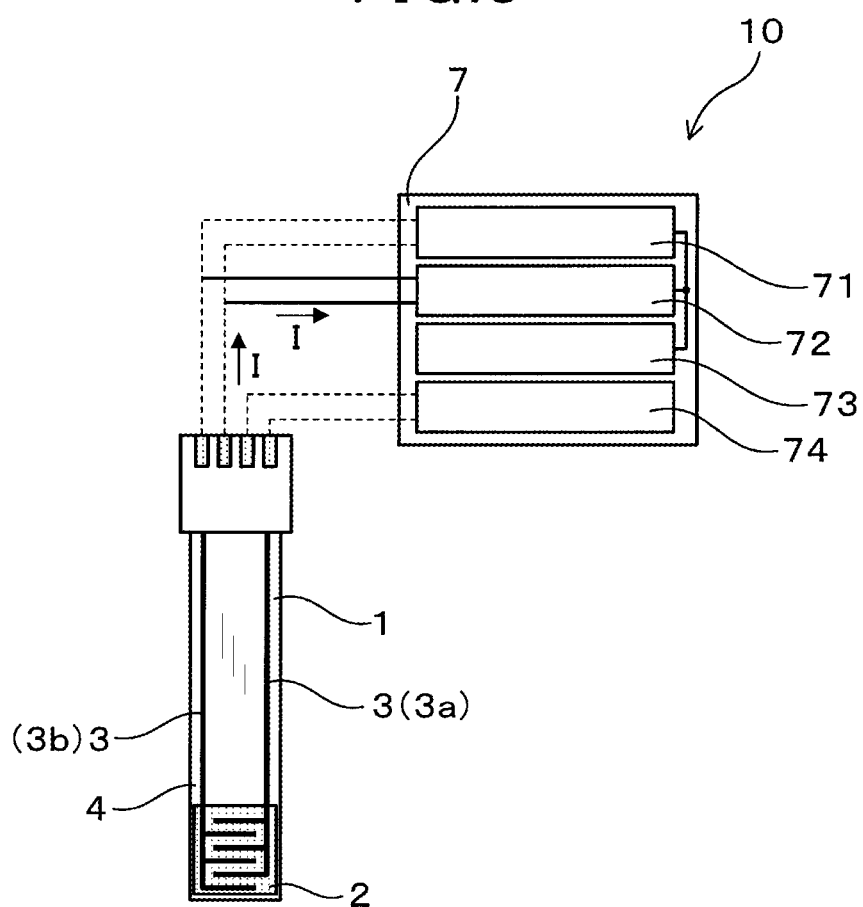
FIG. 8 is a conceptual diagram of a particulate matter detection apparatus of the first embodiment.

Next, a particulate matter detection apparatus 10 that uses the PM sensor 1 will be explained. As illustrated in FIG. 8, the particulate matter detection apparatus 10 includes the PM sensor 1 described above, and a control unit 7 that is connected to the above-described PM sensor 1. The control unit 7 includes a voltage-application unit 71, an electrical-current-measurement unit 72, a calculation unit 73 and a heater-control unit 74. The voltage-application unit 71 applies voltage between the pair of electrodes 3a, 3b. Moreover, the electrical-current-measurement unit 72 measures the electrical current I that flows between the electrodes 3a, 3b. The heater-control unit 74 causes the heater 5 (refer to FIG. 7) to heat up and burn the particulate matter 6 when the large amount of the particulate matter 6 accumulates on the accumulation surface 20 and then the electrical current I becomes saturated. The calculation unit 73 uses a measured value of the electrical current I to calculate the amount of the particulate matter 6 that is accumulated on the accumulation surface 20. Moreover, the calculation unit 73 uses this calculated value and the amount of time required for accumulation of the particulate matter 6 to calculate the amount of particulate matter 6 included in the exhaust gases that is discharged per unit time.

As illustrated in FIG. 9, the PM sensor 1 is provided between the second end of the apparatus A and the cleaning apparatus 17. The amount of particulate matter 6 that is included in the exhaust gases having passed through the cleaning apparatus 17 is calculated using the PM sensor 1 and the control unit 7. The control unit 7 transmits the calculated amount of the discharged particulate matter 6 per unit time to an ECU 16. The ECU 16 is configured so as to determine that there is fault in the cleaning apparatus 17 when the amount of the detected particulate matter 6 exceeds a specified value, and notifies the user and the like.

Next, functions and effects of the present embodiment will be explained. As illustrated in FIG. 2, the PM sensor 1 of the present embodiment includes the conductive part 2 that is formed into a plate shape using a conductive material that has higher electrical resistivity than the particulate matter 6. One major surface S1 of the conductive part 2 is set to be the accumulation surface 20 where particulate matter accumulates. The pair of electrodes 3a, 3b are formed on the accumulation surface 20.

Therefore, it is possible to improve the detection sensitivity for the detecting particulate matter 6. In other words, in the present embodiment, the pair of electrodes 3a, 3b are formed on the accumulation surface 20 of the conductive part 2, as illustrated in FIG. 3, and when a voltage is applied between the electrodes 3a, 3b in a state in which there is absolutely no particulate matter 6 accumulated, it is possible to allow the electrical current I to flow to the accumulation surface 20 instead of inside the conductive part 2. Therefore, as illustrated in FIG. 4, when there is the small amount of the particulate matter 6 accumulated on the accumulation surface 20, it is possible to allow the electrical current I to flow to the particulate matter 6 that has lower electrical resistivity than the conductive part 2, and thus it is possible to increase the current value between the electrodes 3a, 3b. Consequently, even when only the small amount of the particulate matter 6 is accumulated, it is possible to detect the particulate matter 6, and it is possible to increase the detection sensitivity of the particulate matter detection sensor 1.

Figure 27:
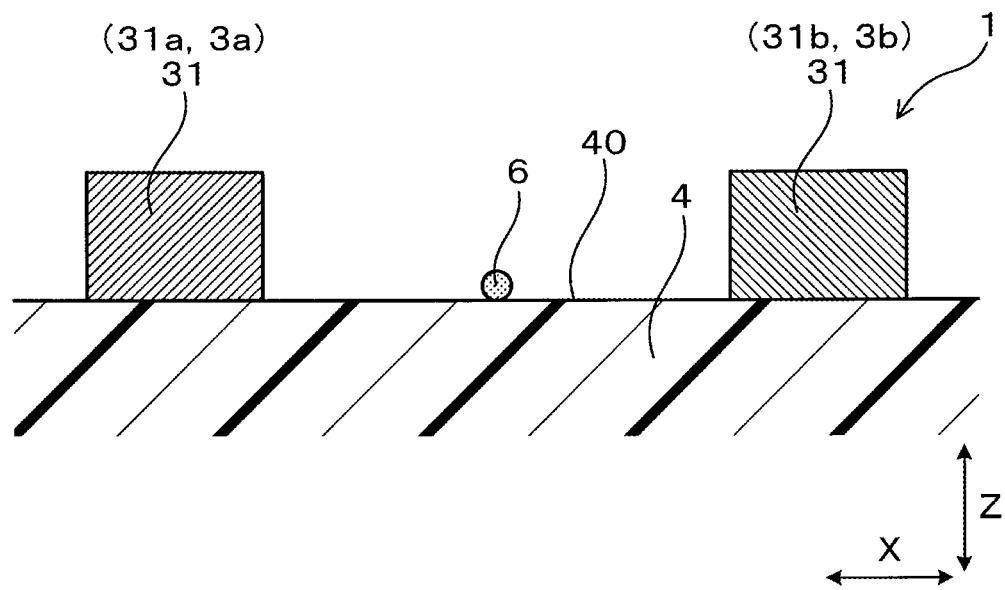
FIG. 27 is an enlarged cross-sectional view of a particulate matter detection sensor in a first comparative embodiment in a state in which only a little particulate matter is accumulated.
Figure 28:
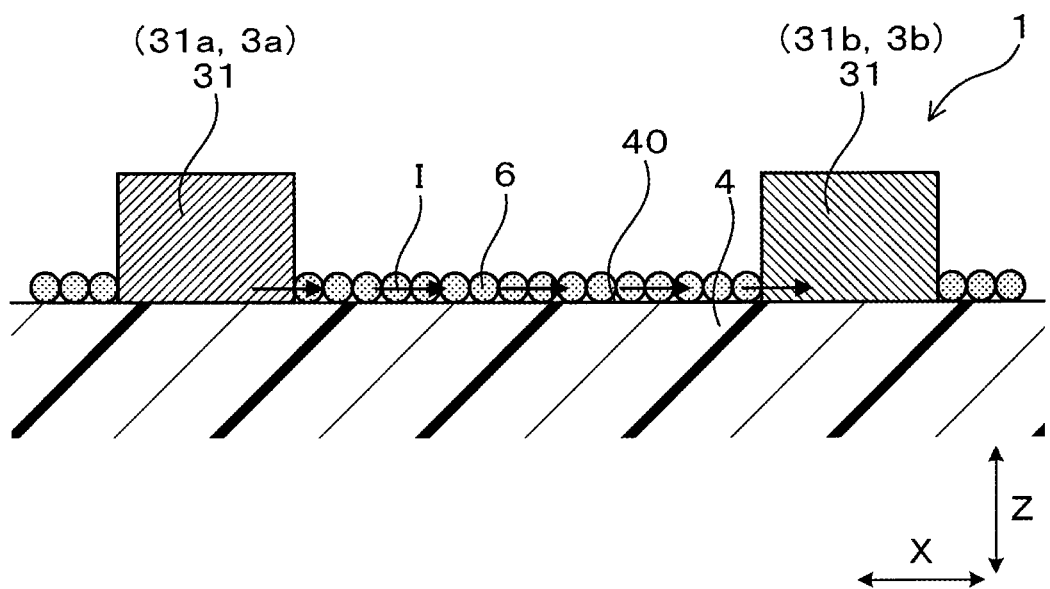
FIG. 28 is an enlarged cross-sectional view of the particulate matter detection sensor in the first comparative embodiment in a state in which more particulate matter is accumulated.
Figure 29:
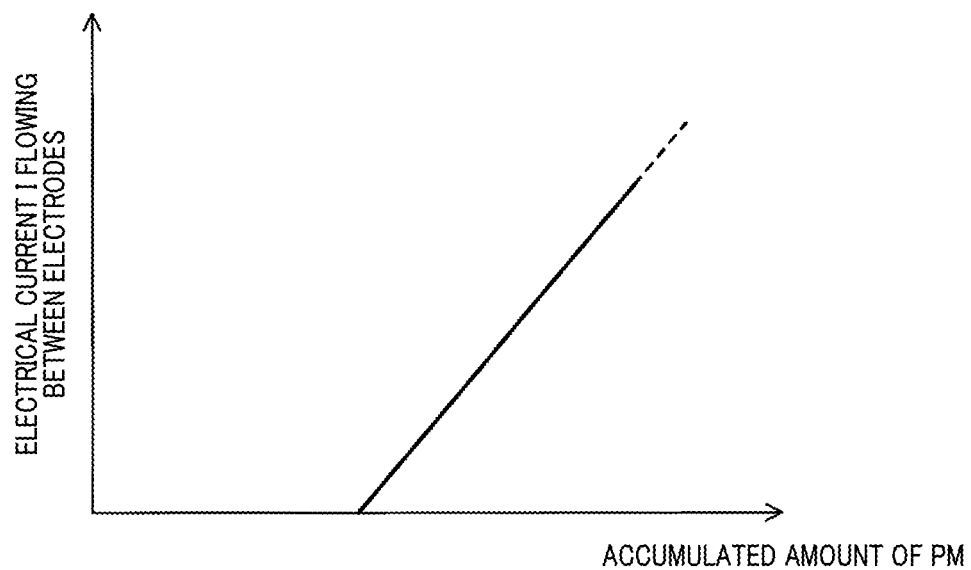
FIG. 29 is a graph illustrating the relationship between the accumulated amount of particulate matter and electrical current in the first comparative embodiment.

Here, supposing, as illustrated in FIG. 27, supposing that the surface of the substrate section 4 that is made of an insulating material such as a ceramic is set to be the accumulation surface 40, and the electrodes 3a, 3b are formed on the accumulation surface 40, a path for the electrical current I is not formed between the electrodes 3a, 3b when only the small amount of the particulate matter 6 is accumulated. Therefore, the electrical current I does not flow between the electrodes 3a, 3b. As illustrated in FIG. 28 and FIG. 29, when a large amount of the particulate matter 6 accumulates and the path for the electrical current I is formed using the particulate matter 6, the electrical current I begins to flow. Therefore, the particulate matter cannot be detected when only the small amount of the particulate matter 6 is accumulated.

Figure 30:
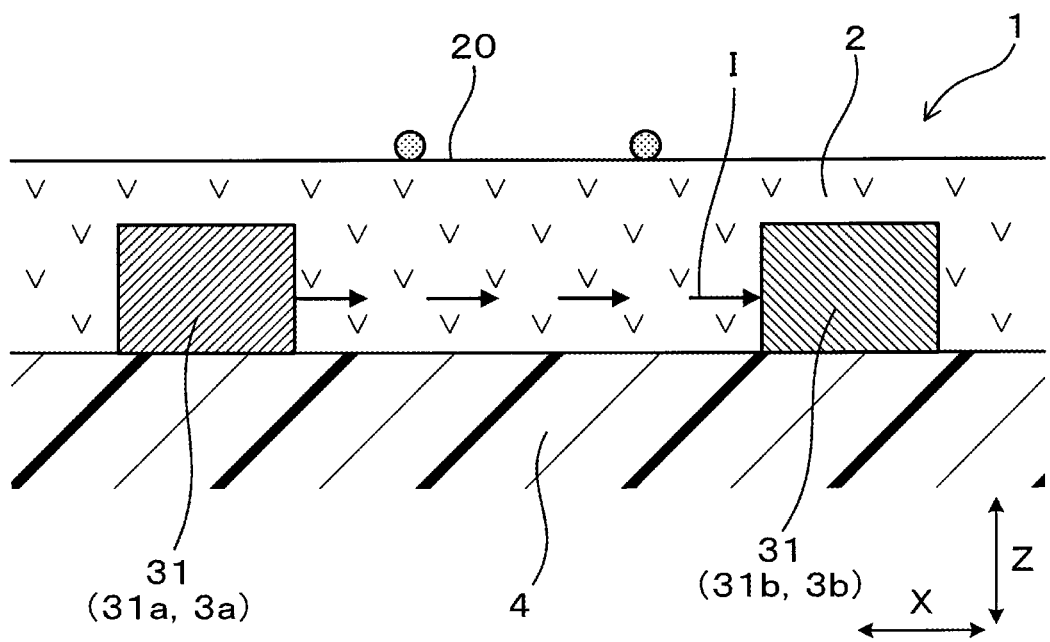
FIG. 30 is an enlarged cross-sectional view of a particulate matter detection sensor in a second comparative embodiment in a state in which only a little particulate matter is accumulated.
Figure 31:
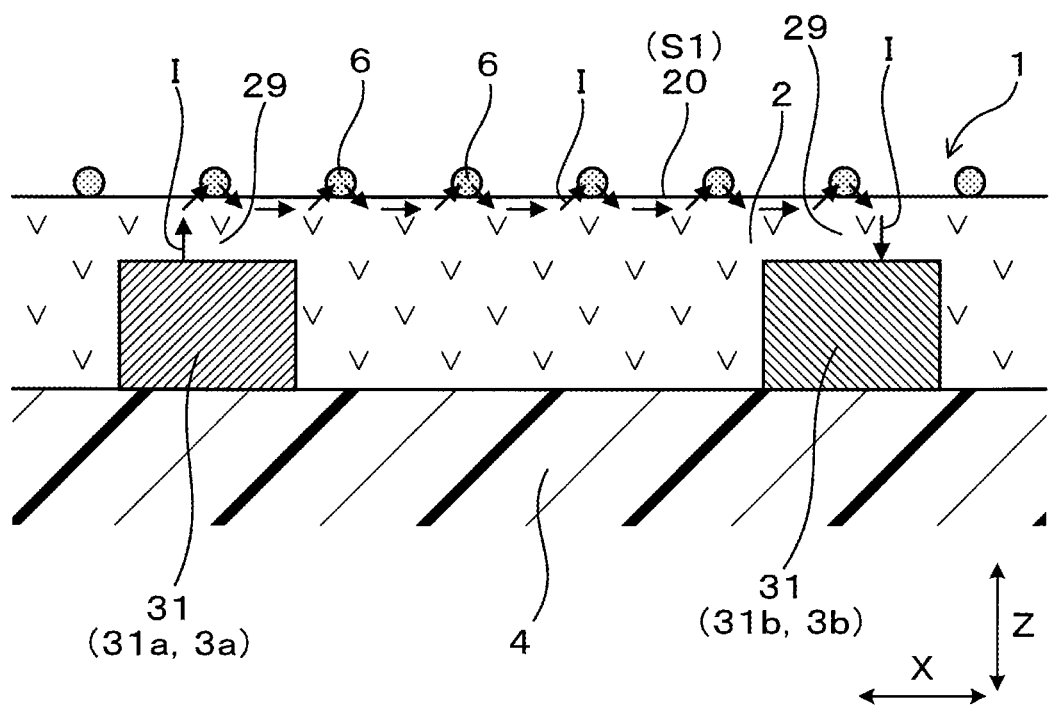
FIG. 31 is an enlarged cross-sectional view of the particulate matter detection sensor in the second comparative embodiment in a state in which more particulate matter is accumulated.

As illustrated in FIG. 30, covering the electrodes 3a, 3b using the conductive part 2 is also feasible, however, in that case, when there is only a small amount of the accumulated particulate matter 6, the electrical current I mainly flows inside the conductive part 2. This PM sensor 1, as illustrated in FIG. 31, is such that the electrical current I flows in the particulate matter 6 after the large amount of the particulate matter 6 accumulates on the accumulation surface 20, and the electrical resistance via the particulate matter 6 becomes less than the electrical resistance inside the conductive part 2. Therefore, it is not possible to detect the particulate matter 6 when there is the small amount of the accumulated particulate matter 6.

However, as illustrated in FIG. 3 to FIG. 5, as the present embodiment, when the surface Si of the conductive part 2 is set to be the accumulation surface 20, and electrodes 3a, 3b are formed on this accumulation surface 20, even when there is absolutely no accumulated particulate matter 6, it is possible for the electrical current I to flow to the accumulation surface 20 of the conductive part 2. Therefore, when a small amount of the particulate matter 6 is accumulated, it is possible for the electrical current I to flow to the particulate matter 6 that has resistivity that is lower than that of the conductive part 2. Consequently, even when there is only the small amount of the particulate matter 6 is accumulated, the current between the electrodes 3a, 3b increases and it is possible to detect that the particulate matter 6 has accumulated. Therefore, it is possible to improve the sensitivity of the PM sensor 1.

Moreover, as illustrated in FIG. 31, when the electrodes 3a, 3b are covered by the conductive part 2, the electrical current I flows though the portion 29 between the electrodes 3a, 3b and the surface S1 (an accumulation surface 20) of the conductive part 2. Therefore, during manufacturing, when variation occurs in the thickness of this portion 29, the resistance value between the electrodes 3a, 3b varies. Hence, the current between the electrodes 3a, 3b varies. Consequently, the accuracy in measuring the particulate matter 6 is likely to decrease.

However, as illustrated in FIG. 2 and FIG. 3, by forming electrodes 3a, 3b on the surface S1 of the conductive part 2 as in the present embodiment, the electrical current I does not flow through the conductive part 2 in a thickness direction (a Z direction) of the PM sensor. Therefore, a problem of variation in the thickness of the conductive part 2 or variation in the electrical resistance does not occur. As a result, variation in the resistance value of the conductive part 2 can be suppressed between the electrodes 3a, 3b and it becomes possible to accurately calculate the amount of particulate matter 6 that accumulates on the accumulation surface 20.

Moreover, the particulate matter detection apparatus 10 includes the PM sensor 1 described above. Therefore, together with being able to increase the detection sensitivity for detecting the particulate matter 6 that is included in exhaust gases, it becomes possible to increase the detection accuracy for detecting particulate matter 6.

Furthermore, as illustrated in FIG. 8 and FIG. 9, in the present embodiment, the control unit 7 measures the electrical current I that flows between the electrodes 3a, 3b of the PM sensor 1.

In doing so, it is possible to more accurately measure the amount of particulate matter 6. In other words, it is also possible to measure the electrical current I in the PM sensor 1 using the ECU 16, however, in that case, the distance from the PM sensor 1 to the ECU 16 is long, so that noise may be mixed into the electrical current I in the PM sensor. However, by measuring the electrical current I using the control unit 7 that is arranged near the PM sensor 1, it is unlikely that noise is mixed into the electrical current I in the PM sensor. Therefore, it is possible to more accurately measure the amount of the particulate matter 6 that is included in the exhaust gases.

Moreover, as illustrated in FIG. 1, the electrodes 3 of the present embodiment includes the common sections 30, and the comb-tooth sections 31 that extend respectively from the common sections 30. As illustrated in FIG. 2, the width W of each of the comb-tooth sections 31 in the X direction of the PM sensor is set to be shorter than the width W' of the space between the comb-tooth sections 31.

Therefore, it is possible to sufficiently shorten the width W of the comb-tooth section 31. Consequently, in the X direction of the PM sensor, the length of the portion between two comb-tooth sections 31*a*, 31*b* that are adjacent to each other, or in other words, the portion where particulate matter can be detected can be made long. Therefore, it is possible to increase the probability that the particulate matter 6 will adhere, and thus it is possible to increase the detection sensitivity of the PM sensor.

Moreover, the conductive material of the conductive part 2 described above contains the metal oxide having electrical conductivity.

The metal oxide has high heat resistance. Therefore, using the conductive material described above, it is possible to increase the heat resistance of the conductive part 2.

Furthermore, using the conductive material described above, it is possible to further increase the accuracy in measuring the particulate matter 6. In other words, the electrical resistance of the particulate matter 6 greatly changes depending on the temperature. Therefore, when calculating the amount of particulate matter 6 accumulated from the electrical current I that flows between the electrodes 3*a*, 3*b*, it is necessary to perform temperature correction. The electrical resistance of the particulate matter 6 decreases as the temperature rises. Moreover, the electrical resistance of the conductive material containing the metal oxide also decreases as the temperature rises. Consequently, using the conductive material described above as the conductive part 2, it is possible to balance the temperature characteristics of the electrical resistance of the conductive part 2 and the particulate matter 6, and thus it becomes easier to perform temperature correction. Therefore, it is possible to further increase the accuracy in measuring the particulate matter 6.

As illustrated in FIG. 2, in the present embodiment, the substrate section 4 made of the insulating material is arranged on one of the faces of the conductive part 2 facing each other, and the accumulation surface 20 is formed on the other one of the faces of the conductive part 2. The heater 5 is provided in the substrate section 4.

Therefore, it is possible to reduce power consumption of the heater 5. In other word, instead of providing the substrate section 4, it is also possible to provide the heater 5 inside the conductive part 2 (refer to FIG. 10), however, in that case, it is necessary to maintain the overall rigidity of the PM sensor 1 by the conductive part 2 itself, so it becomes necessary to make the thickness of the conductive part 2 sufficiently thick. Moreover, the conductive material of the conductive part 2 is selected by preferentially considering material having superior resistivity and temperature characteristics, so it is not always possible to use a material that has superior thermal conductivity. Therefore, it becomes difficult to heat the accumulation surface 20 by the heater 5, and it becomes easy for the power consumption by the heater 5 to increase. However, as illustrated in FIG. 2, by providing the substrate section 4, the rigidity can be maintained by the substrate section 4, so it is possible to make the thickness of the conductive part 2 thin. Moreover, it is possible to select a material having excellent thermal conductivity as the material of the substrate section 4, so it becomes easy to heat the accumulation surface 20 using the heater 5. Therefore, it is possible to reduce the power consumption of the heater 5.

As described above, with the present embodiment, it is possible to provide the particulate matter detection sensor and the particulate matter detection apparatus which uses the particulate matter detection sensor capable of increasing the detection sensitivity and the detection accuracy for detecting particulate matter.

In the embodiments below, of the reference numbers used in the drawings, the reference numbers that are the same as those used in the first embodiment, indicate components that are the same as in the first embodiment unless stated otherwise.

(Second Embodiment)

Figure 10:
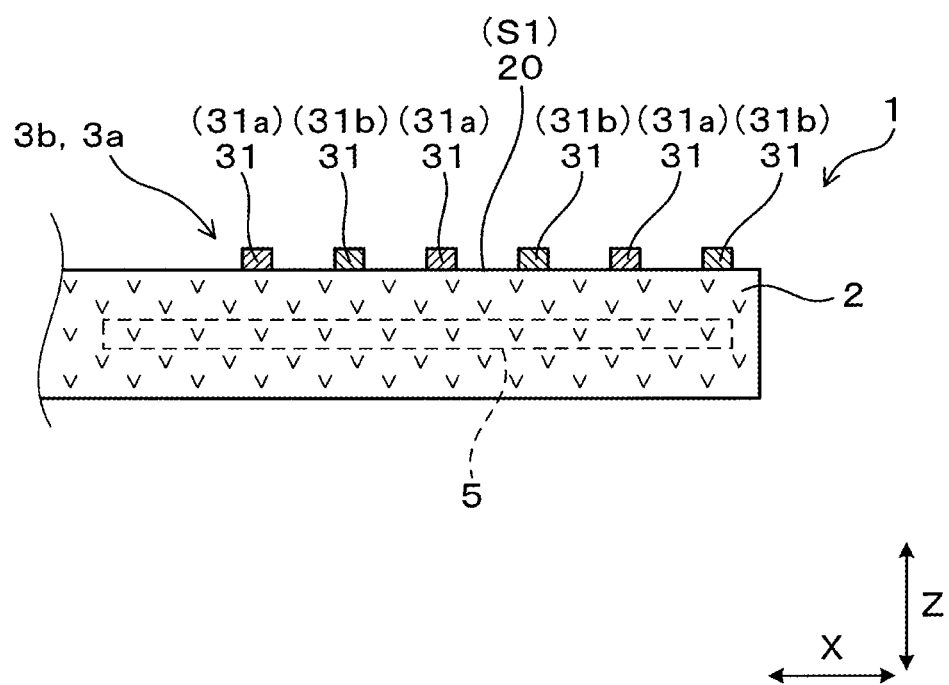
FIG. 10 is a cross-sectional view of a particulate matter detection sensor of a second embodiment.

The present embodiment is an example in which an arrangement position of a heater 5 is changed. As illustrated in FIG. 10, the present embodiment differs from the first embodiment in that a substrate section 4 is not used. In the present embodiment, the heater 5 is provided in a conductive part 2. One surface S1 of this conductive part 2 is set to be an accumulation surface 20. A pair of electrodes 3*a*, 3*b* is formed on this accumulation surface 20.

The effect of the present embodiment will be explained below. In the present embodiment, the substrate section 4 is not used, so it is possible to reduce the number of parts in a PM sensor 1. Therefore, it is possible to reduce the manufacturing cost of the PM sensor 1. Moreover, as in the first embodiment, when layering the conductive part 2 and the substrate section 4, since the respective thermal expansion coefficients differ, there is a possibility that warping of the PM sensor 1, peeling of the conductive part 2, and the like will occur, when the heater 5 is heated. However, in the present embodiment, the substrate section 4 is not used, and such problems are unlikely to occur.

The other configuration and effects are the same as those in the first embodiment.

(Third Embodiment)

Figure 11:
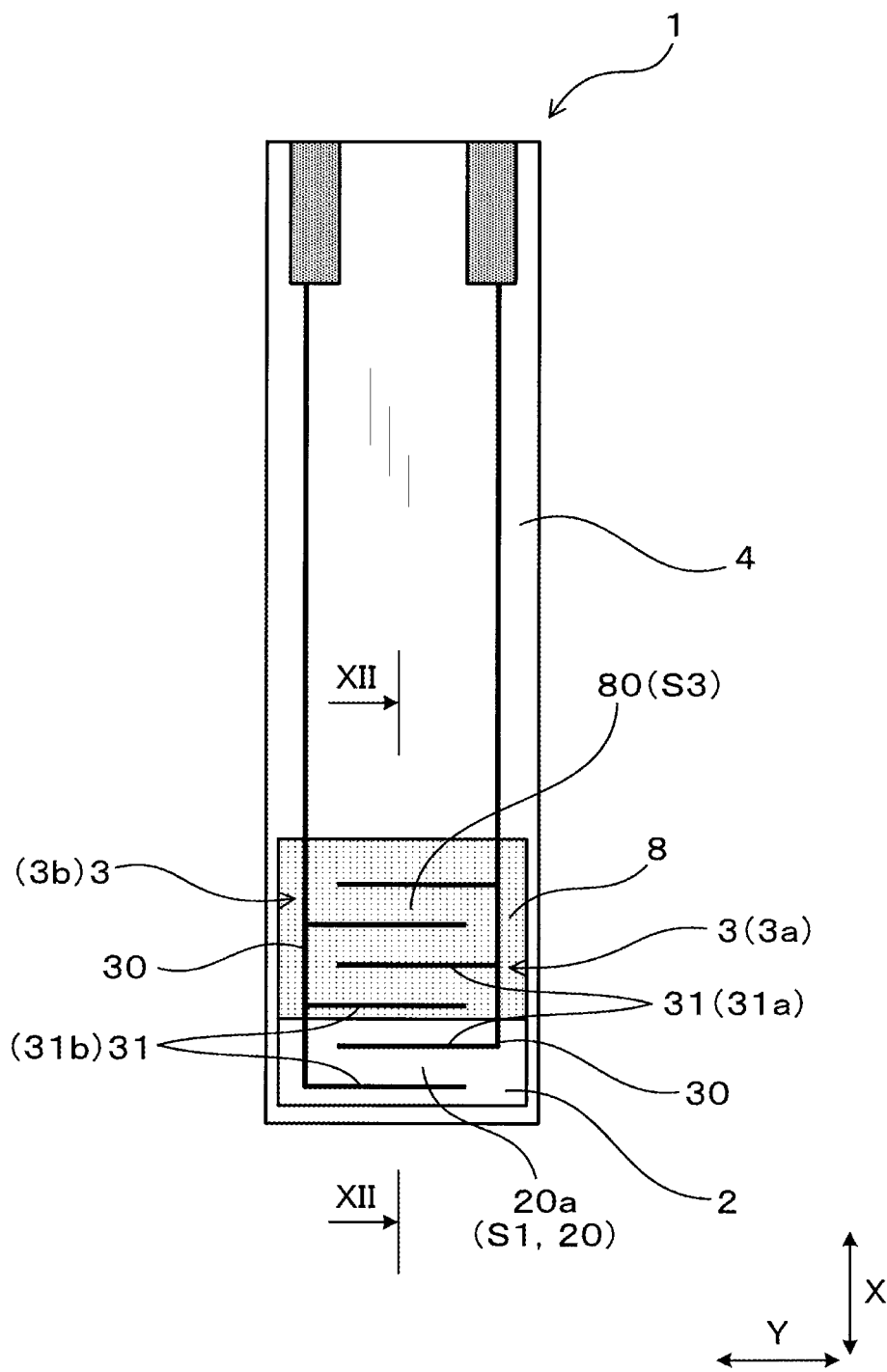
FIG. 11 is a plan view of a particulate matter detection sensor of a third embodiment, and is a view seen from an arrow direction XI in FIG. 12.
Figure 12:
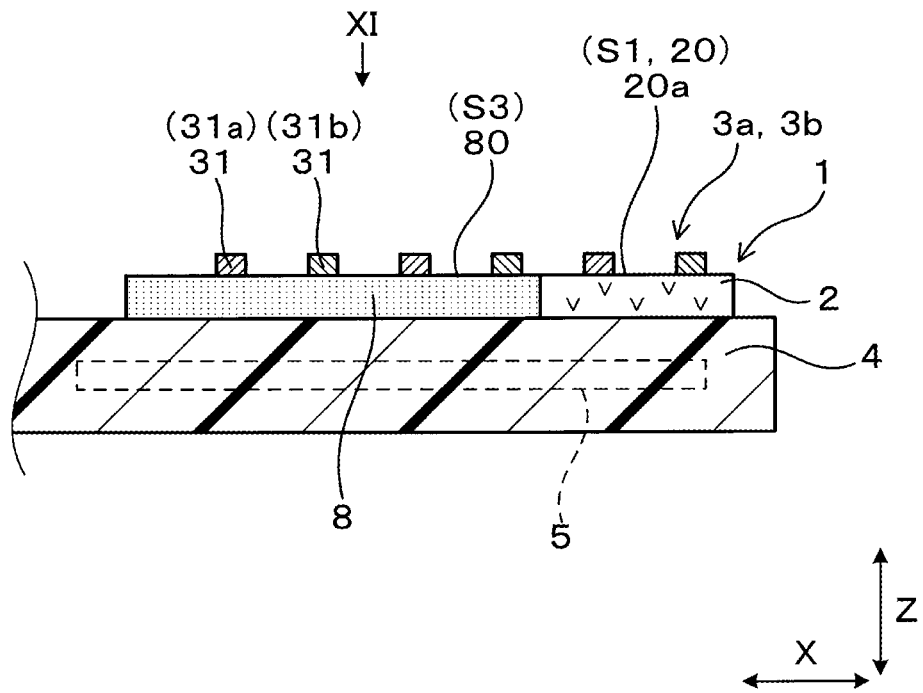
FIG. 12 is a cross-sectional view taken along a line XII-XII in FIG. 11.

The present embodiment is an example in which a surface area of a conductive part 4 is reduced. As illustrated in FIG. 11 and FIG. 12, in the present embodiment, the area of the conductive part 4 is smaller than that in the first embodiment. A surface S1 of this conductive part 4 is set to be a conductive-side accumulation surface 20*a* where particulate matter 6 accumulates.

Moreover, a plate shaped insulating section 8 that is made of an insulating material is arranged in a position adjacent to a conductive part 4 in an X direction of a PM sensor. A surface S3 of this insulating section 8 that is on the opposite from the side that comes into contact with the substrate section 4 is set to be an insulating-side accumulation surface 80 on which particulate matter 6 accumulates. The pair of electrodes 3*a*, 3*b* are formed over a conductive-side accumulation surface 20*a* formed on a conductive part 2 and an insulating-side accumulation surface 80. The surface area of the conductive-side accumulation surface 20a is less than the surface area of the insulating-side accumulation surface 80.

An electrodes 3a, 3b, as in the first embodiment, include common sections 30 and comb-tooth sections 31 that protrude respectively from the common sections 30. The number of comb-tooth sections 31 that are formed on a conductive-side accumulation surface 20a is less than the number of comb-tooth sections 31 that are formed on an insulating accumulation surface 80.

Figure 13:
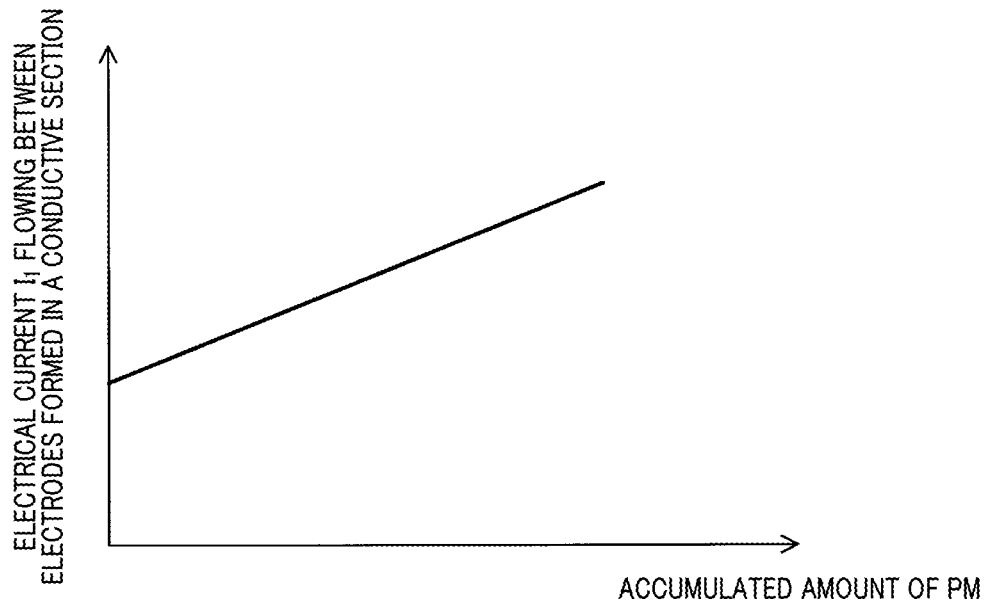
FIG. 13 is a graph illustrating the relationship between the amount of particulate matter accumulated in a conductive part and the electrical current that flows between comb-like teeth that are formed in the conductive part in the third embodiment.

As in the first embodiment, the conductive part 2 is made of a conductive material, so an electrical current $I_1$ flows between the comb-tooth sections 31a, 31b that are formed on the conductive-side accumulation surface 20a even when only a small amount of particulate matter 6 is accumulated on a conductive-side accumulation surface 20a. Therefore, the relationship between the amount of the particulate matter 6 that accumulates on the conductive-side accumulation surface 20a and the electrical current $I_1$ is as illustrated by the graph in FIG. 13.

Figure 14:
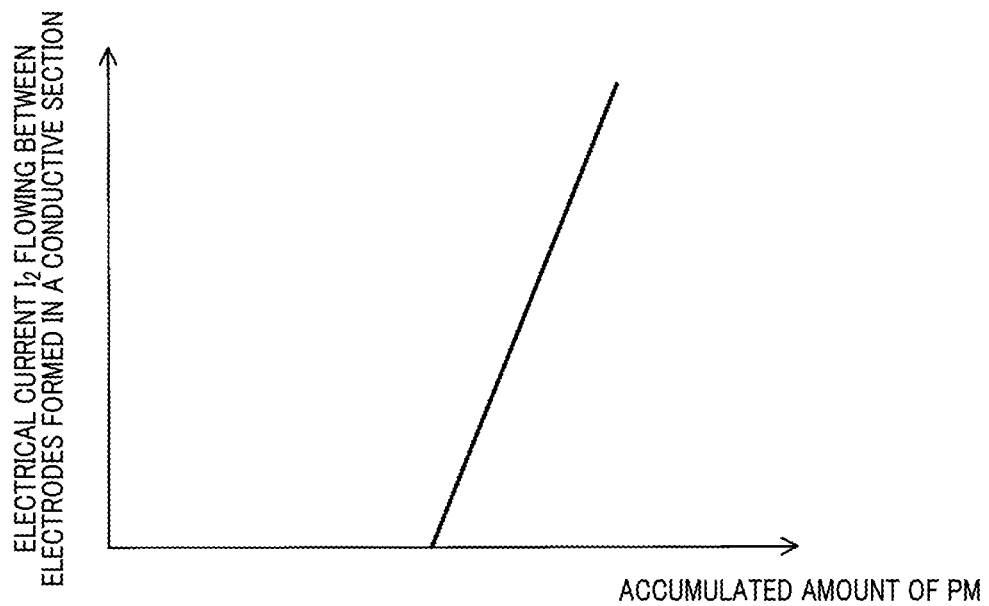
FIG. 14 is a graph illustrating the relationship between the amount of particulate matter accumulated in an insulating section and the electrical current that flows between comb-like teeth that are formed in the insulating section in the third embodiment.

Moreover, the insulating section 8 is made of an insulating material, so electrical current $I_2$ does not flow when only the small amount of the particulate matter 6 is accumulated on the insulating-side accumulation surface 80, however, as in a normal electrical resistance type sensor that does not use a conductor, an electrostatic force occurs between the electrodes, and this insulating section 8 has a function of causing particulate matter 6 to be arranged along the electrostatic field. When a conductive path is formed as the particulate matter 6 becomes arranged between the comb-tooth sections 31a, 31b on the insulating-side accumulation surface 80 due to an effect of an electrostatic force, an electrical current $I_2$ flows between these comb-tooth sections 31a, 31b. Therefore, the relationship between the amount of particulate matter 6 that accumulates on the insulating-side accumulation surface 80 and the electrical current $I_2$ becomes as illustrated by the graph in FIG. 14. The conductive path that is formed between the comb-tooth sections 31a, 31b of the insulating-side accumulation surface 80 is formed only by the particulate matter 6, and because the electrical resistance of the particulate matter 6 is low, a large amount of current flows between these comb-tooth sections 31a, 31b. Therefore a slope of a graph becomes steeper than the graph in FIG. 13.

Figure 15:
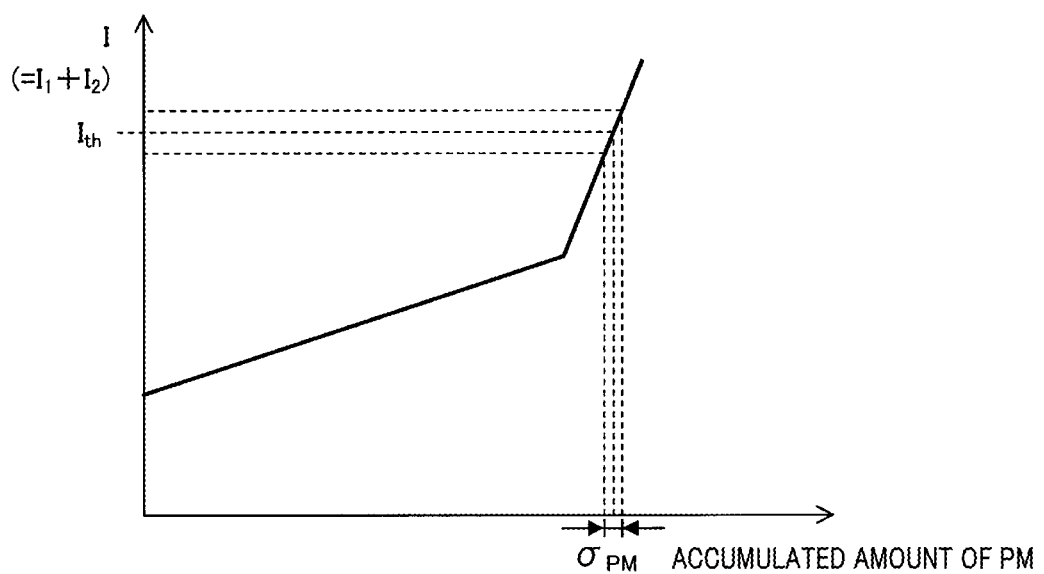
FIG. 15 is a graph obtained by adding FIG. 13 to FIG. 14.

The relationship between the amount of the particulate matter 6 that is accumulated on the two accumulation surfaces 20a, 80 and the electrical current I ($=I_1+I_2$) that flows between the pair of electrodes 3a, 3b becomes as illustrated by the graph in FIG. 15. This graph is a combination of the graphs in FIG. 13 and FIG. 14. As illustrated in FIG. 15, until the comb-tooth sections 31a, 31b that are formed on the insulating-side accumulation surface 80 are connected using the particulate matter 6, the slope of the electrical current I of a graph in FIG. 15 is small, thereafter, the slope of the electrical current I of the graph in FIG. 15 becomes large. Moreover, in the present embodiment, when a lot of particulate matter 6 accumulates and the electrical current I that flows between the electrodes 3a, 3b exceeds a preset threshold value $I_{th}$, the heater 5 is set to heat and burns the particulate matter 6. The electrical current I reaches the threshold current $I_{th}$ after the slope of the graph in FIG. 15 becomes large.

The effect of the present embodiment will be explained below. The PM sensor 1 of the present embodiment includes a conductive part 2 and insulating section 8, and the pair of electrodes 3a, 3b are formed over the conductive part 2 and the insulating section 8. Therefore, even when there is only a little particulate matter 6 accumulated on the conductive part 2, current I flows between the electrodes 3a, 3b, and it is possible to detect the amount of the accumulated particulate matter 6. Moreover, a particulate matter detection apparatus 10 of the present embodiment is configured such that when a lot of particulate matter 6 accumulates on the PM sensor 1, the slope of the electrical current I of the graph in FIG. 15 becomes steep, and when the electrical current I exceeds a threshold value $I_{th}$, the particulate matter 6 is burned. Therefore, it is possible to reduce the variation GPM of the particulate matter 6 when the electrical current I reaches the threshold value $I_{th}$. Consequently, it becomes easy to burn the particulate matter 6 at a suitable timing.

The other configuration and effects are the same as in the first embodiment.

(Fourth Embodiment)

Figure 18:
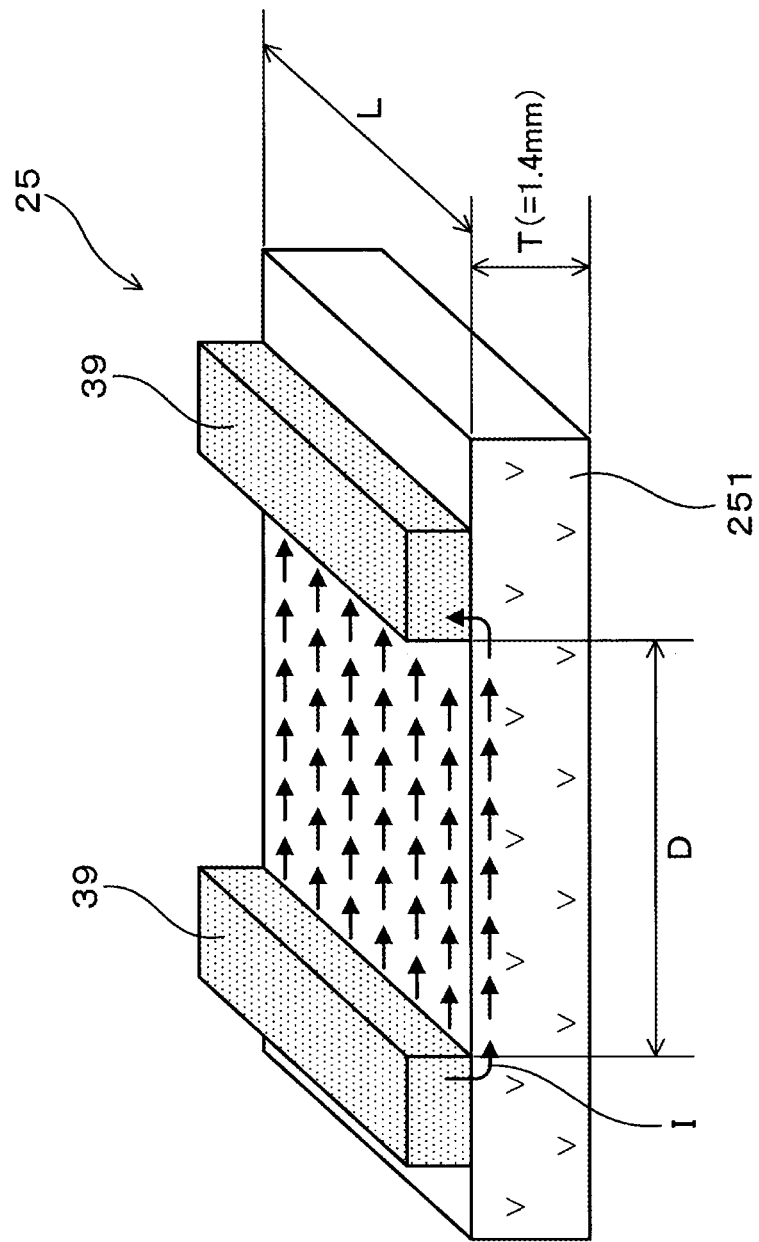
FIG. 18 is a diagram for explaining a measurement method for measuring the surface electrical resistivity $\rho$ in a fourth embodiment.

The present embodiment is an example in which a conductive material of a conductive part 2 is changed. In the present embodiment, as will be described below, a surface electrical resistivity p of the conductive material is measured. In other words, first, a sample 25 as illustrated in FIG. 18 is prepared. The sample 25 has a plate-shaped substrate 251 that is made using a conductive material having a thickness T of 1.4 mm, and a pair of measurement electrodes 39 that are formed on the major surface of the plate-shaped substrate 251 and that have length L and are separated by a space D. Such a sample 25 is made, and an electrical resistance R (Ω) between the pair of measurement electrodes 39 is measured. The surface electrical resistivity ρ is calculated by the following equation (1).

$$\rho = R \times L \times T/D \qquad (1)$$

Figure 21:
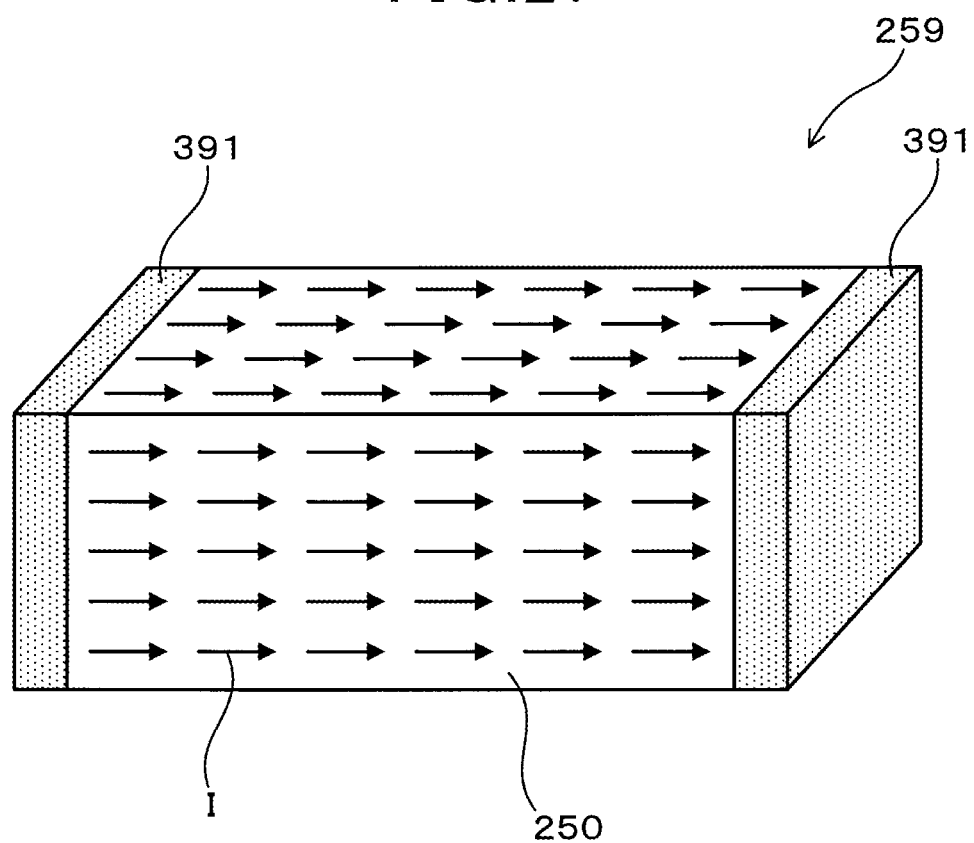
FIG. 21 is a diagram for explaining a method for measuring the electrical resistivity of bulk in a fourth embodiment.

In this specification, when the resistivity is described as simply "electrical resistivity", it means the so-called bulk electrical resistivity. This can be calculated as illustrated in FIG. 21 by making a bulk sample 259 that includes a substrate section 250 that is made using a conductive material, and a pair of measurement electrodes 391 that are formed on the side surface of the substrate section 250, and measuring the electrical resistance between the pair of measurement electrodes 391. Moreover, when the resistivity is described as "surface electrical resistivity ρ", it means a value that obtained by making a sample 25 as illustrated in FIG. 18, and measuring the electrical resistance R between the measurement electrodes 39, and calculating the value using Equation (1) described above.

Figure 16:
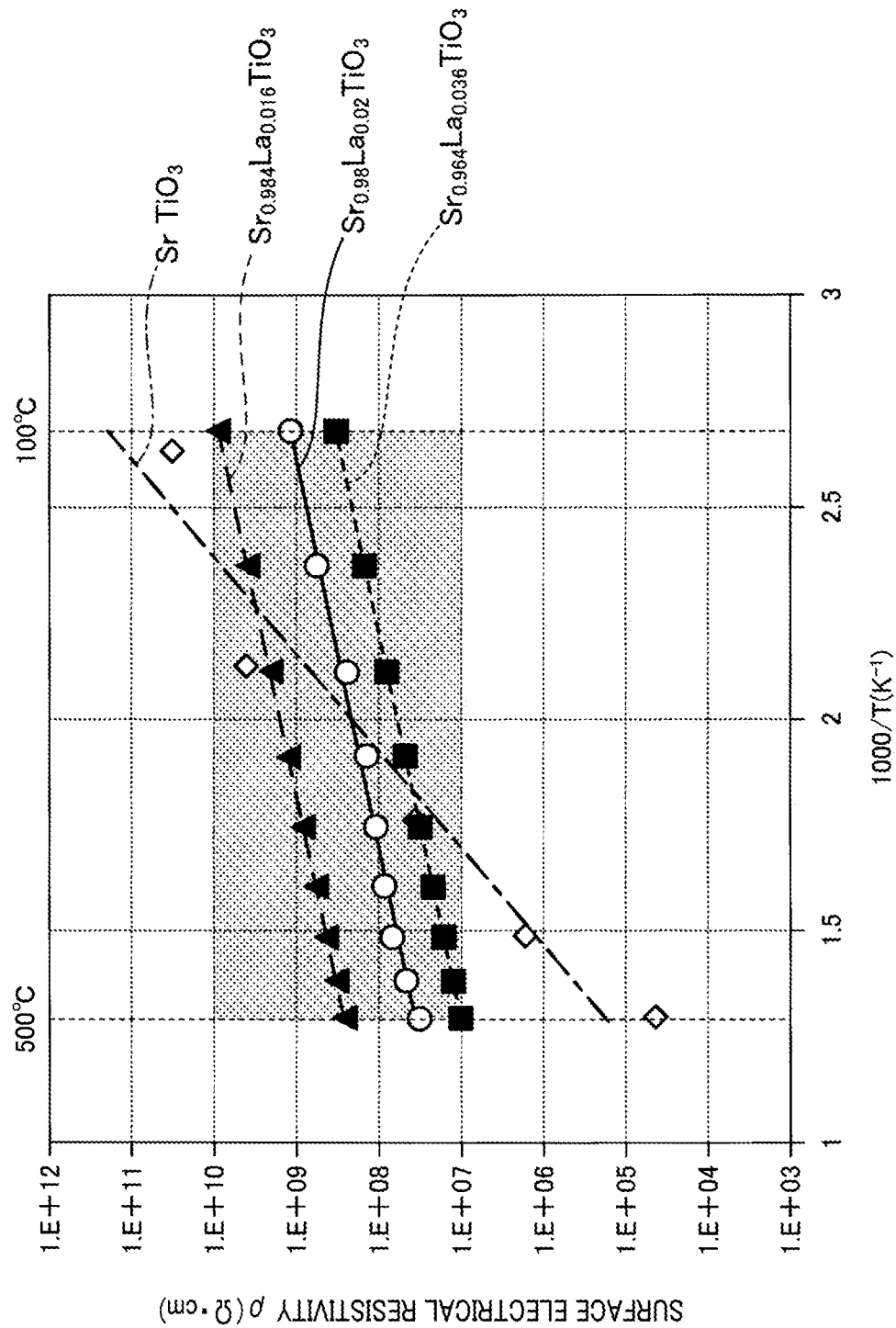
FIG. 16 is a graph illustrating the relationship between the surface electrical resistivity $\rho$ and temperature of $Sr_{1-x}La_x$-$TiO_3$ in a fourth embodiment.

Moreover, in the present embodiment, as illustrated in FIG. 16, the conductive part 2 is formed using a conducive material of which the surface electrical resistivity ρ is $1.0 \times 10^7$ to $1.0 \times 10^{10}$ Ω·cm in a temperature range of 100° C. to 500° C.

As a conductive material of which the surface electrical resistivity ρ satisfying the above-described numerical range, it is possible to use ceramics having a perovskite structure that is expressed by the molecular formula $ABO_3$. As A in the molecular formula described above, it is possible to use, for example, at least one element selected from among La, Sr, Ca and Mg, and as B described above, it is possible to use at least one element selected from among Ti, Al, Zr and Y.

In the present embodiment, the main component of A in the molecular formula described above is set to be Sr, and the accessory component is set to be La. Moreover, B in the molecular formula described above is set to be Ti. FIG. 16 illustrates a relationship between the surface electrical resistivity ρ and a temperature of this ceramic ($Sr_{1-x}La_xTiO_3$). As illustrated in FIG. 16, when X is set to be 0.016 to 0.036, the surface electrical resistivity ρ of $Sr_{1-x}La_xTiO_3$ becomes $1.0 \times 10^7$ to $1.0 \times 10^{10}$ Ω·cm in the temperature range of 100° C. to 500° C. Therefore, this ceramic can be suitably used as the material of the conductive part 2.

Moreover, as illustrated in FIG. 16, when La is not added to the conductive material ($SrTiO_3$), the surface electrical resistivity ρ becomes approximately $1.0 \times 10^5$ to $1.0 \times 10^{11}$ Ω·cm in the temperature range of 100° C. to 500° C. From this, it can be seen that when La is included in the ceramic described above, there is little change in the surface electrical resistivity ρ due to a temperature.

More specifically, in obtaining the graph in FIG. 16, measurement of the surface electrical resistivity ρ is performed as described below. That is, ceramics were made in which X in $Sr_{1-x}La_xTiO_3$ was 0, 0.016, 0.02, 0.36, and samples 25 (refer to FIG. 18) were made using these ceramics. Each sample 25 includes a plate-shaped substrate 251 having a thickness T of 1.4 mm, and a pair of measurement electrodes 39 that are formed on the major surface of the plate-shaped substrate 251 having a length L of 16 mm and separated by a space D of 800 μm. The samples 25 were then heated in an air atmosphere to 100° C. to 500° C., a voltage of 5 to 1000V was applied between the measurement electrodes 39, and the electrical resistance R was measured. Then, using Equation (1) described above, the surface electrical resistivity ρ was calculated.

Figure 17:
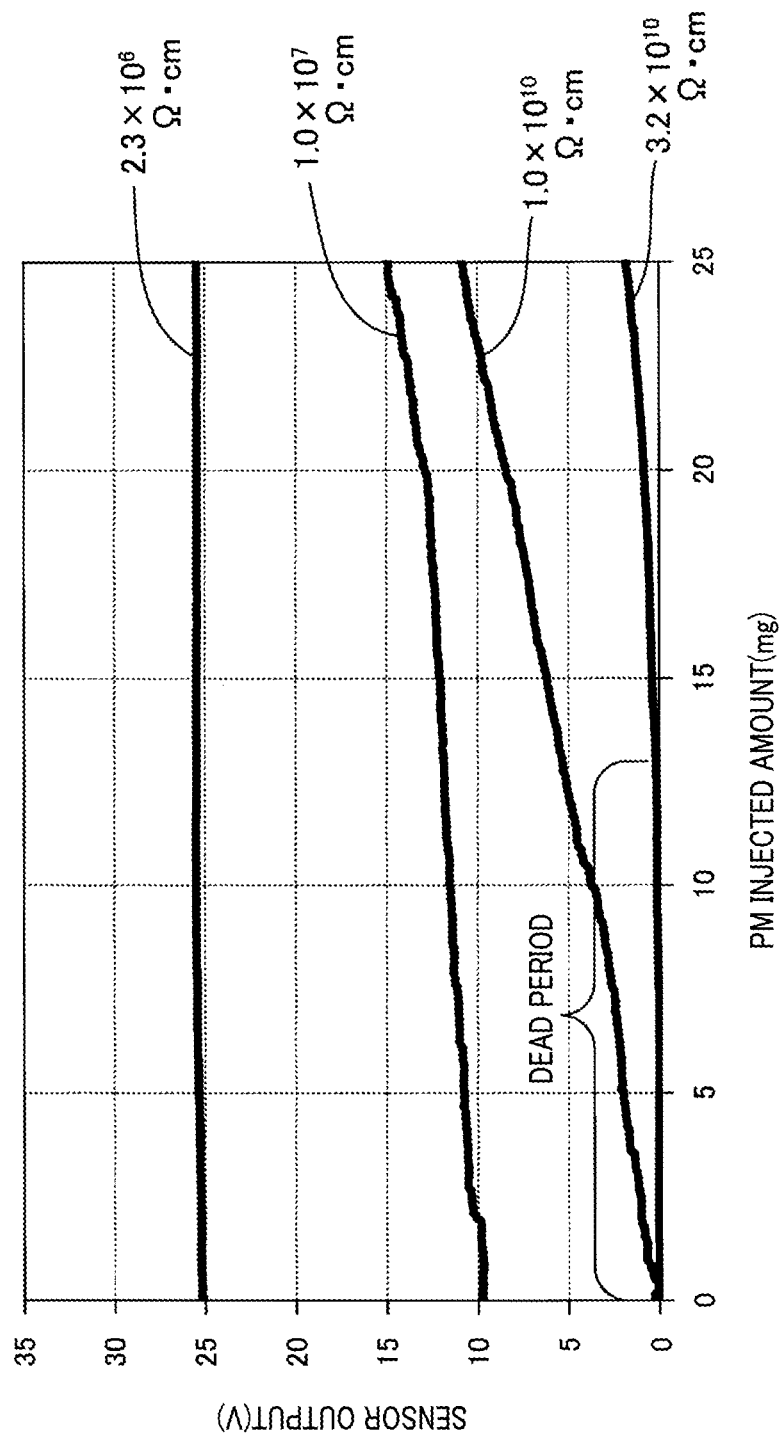
FIG. 17 is a graph that examines the relationship between the PM injection amount and sensor output for plural PM sensors having different surface electrical resistivity $\rho$ of the conductive part in the fourth embodiment.

FIG. 17 illustrates a graph that illustrates the relationship between the amount of PM injected in a PM sensor 1 and the sensor output of the PM sensor 1 when the surface electrical resistivity ρ of the conductive part 2 is changed. This graph is obtained in the following way. First, conductive parts 2 were formed using conductive material having surface electrical resistivity ρ of $2.3 \times 10^6$, $1.0 \times 10^7$, $1.0 \times 10^{10}$, $3.2 \times 10^{10}$ Ω·cm, respectively, and PM sensors 1 were made that included these conductive parts 2. Exhaust gases having a PM content of 0.01 mg/l was injected into each of the PM sensors 1, and a part of this injected PM is accumulated on the accumulation surface 20 of the PM sensors 1. Moreover, an electrical current I flowing between the pair of electrodes 3a, 3b was converted into a voltage using shunt resistor, and the sensor output was obtained. The space between the electrodes 3a, 3b was 80 μm, the applied voltage was 35V, and the measurement temperature was 200° C. FIG. 17 is a graph illustrating the relationship between the injected amount of PM and the sensor output.

As illustrated in FIG. 17, when the surface electrical resistivity ρ of the conductive part 2 is $1.0 \times 10^7$ to $1.0 \times 10^{10}$ Ω·cm, the sensor output of the PM sensor 1 rises even when only a small amount of PM is accumulated. In other words, it can be seen that the sensitivity of the PM sensor 1 is high. Moreover, as PM adheres to the sensor, the sensor output changes greatly. Therefore, it can be seen that as long as the surface electrical resistivity ρ of the conductive part 2 is within the range described above, the sensitivity of the PM sensor 1 is high, and it is possible to accurately measure the amount of accumulated PM.

However, when the surface electrical resistivity ρ is outside of the range described above, it is not possible to sufficiently obtain this kind of effect. For example, when the surface electrical resistivity ρ is $3.2 \times 10^{10}$ Ω·cm and there is only a small amount of PM accumulated, the sensor output does not rise much. In other words, there is a dead period. This is because the surface electrical resistivity ρ of the conductive part 2 is too high, and it is not easy for electrical current I to flow between the electrodes 3a, 3b, and it is thought that electrical current I will only start flowing after a lot of PM is accumulated and a path for electrical current is formed by the PM.

Moreover, when the surface electrical resistivity ρ is $2.3 \times 10^6$ Ω·cm for example, there is hardly any change in the sensor output even when the amount of accumulated PM changes. It is considered that this is because the surface electrical resistivity ρ is too low, and even though PM accumulates, very little electrical current I flows in the PM, and thus it is difficult for the current between the electrodes 3a, 3b to change. Therefore, it is seen that in this case, it is difficult to accurately measure the amount of accumulated PM.

Figure 19:
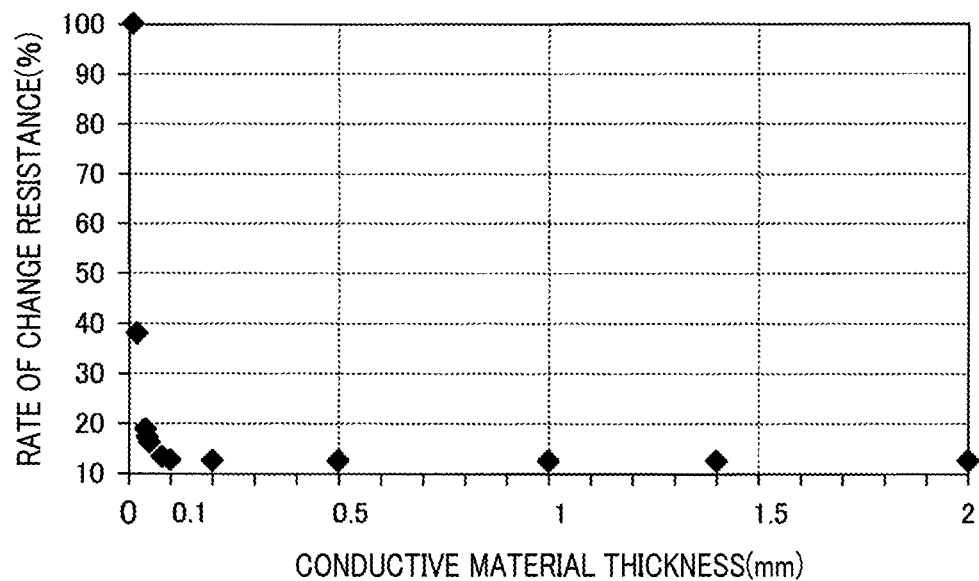
FIG. 19 is a graph illustrating the relationship between the thickness and the electrical resistance of samples in a fourth embodiment.

Next, FIG. 19 will be used to explain the depth from the surface of the electrical current I that flows in the sample 25 (refer to FIG. 18). The graph in FIG. 19 is created as described below. First, conductive material was formed into a sheet shape, measurement electrodes 39 were printed on the surface thereof, and baked to make samples 25. The condition of the thicknesses T of the samples 25 were changed, such as 10 μm, 20 μm, 40 μm, 45 μm, 50 μm, 80 μm, 0.1 mm, 0.2 mm, 0.5 mm, 1.0 mm, 1.4 mm and 2.0 mm. To remove the effect of moisture, these samples 25 were heated to 200° C., a voltage of 500 V was applied between the pair of measurement electrodes 39, and the electrical resistance R was measured. The length L of the measurement electrodes 39 is 16 mm, and the space D in between is 800 μm. Taking the electrical resistance when the thickness of the sample 25 is 10 μm to be a reference (in other words, 100%), a graph illustrating the relationship between the percentage of electrical resistance R of each of the samples with respect to this, and the sample thickness was made.

As illustrated in FIG. 19, when the thickness of the sample 25 is in the range 10 μm to 0.1 mm, the electrical resistance decreases as the thickness increases, however, after the thickness exceeds 0.1 mm, there is hardly any change in the electrical resistance. From this it can be seen that electrical current I only flows to a depth of 0.1 mm from the surface of the sample 25. In the present embodiment, when measuring the surface electrical resistivity ρ, the thickness T of the sample 25 is set to be 1.4 mm. Therefore, a thickness sufficient for electrical current I to flow is maintained.

Figure 20:
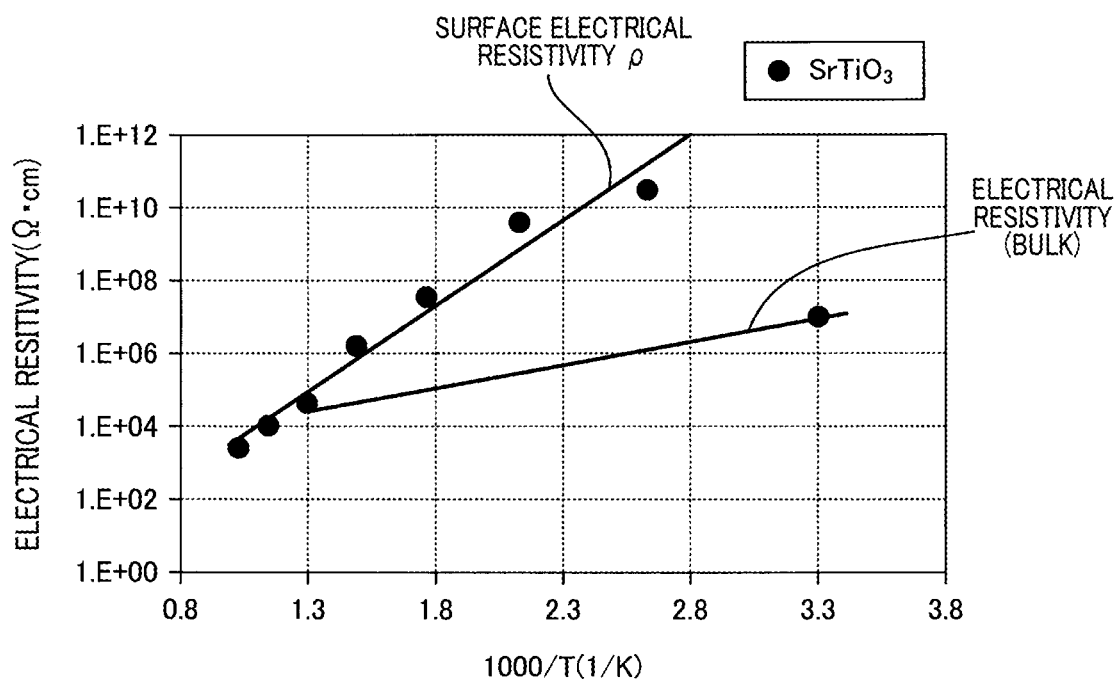
FIG. 20 is a graph that examines the relationship between the conductivity and temperature of $SrTiO_3$ in a fourth embodiment when the measurement method for measuring the conductivity is changed.

Next, the relationship between the electrical resistivity and surface electrical resistivity ρ of $SrTiO_3$ will be explained using FIG. 20. The graph in FIG. 20 is prepared as described below. That is, samples 25 (refer to FIG. 18) were made using $SrTiO_3$, and the surface electrical resistivity ρ was measured while changing the temperature. Moreover, bulk sample 259 (refer to FIG. 21) were made using $SrTiO_3$, and the bulk electrical resistivity was measured while changing the temperature. The relationship between the measured electrical resistivity, surface electrical resistivity ρ and the temperature is illustrated in the graph in FIG. 20. From FIG. 20, it can be seen that values of the bulk electrical resistivity and the surface electrical resistivity ρ are completely different.

Next, the effect of the present embodiment will be explained. In the present embodiment, a conductive part 2 was formed using a conductive material having a surface electrical resistivity ρ that is $1.0 \times 10^7$ to $1.0 \times 10^{10}$ Ω·cm in a temperature range of 100° C. to 500° C.

Therefore, as illustrated in FIG. 17, there is little dead period, and it is possible to obtain a PM sensor 1 of which the sensor output greatly changes as particulate matter adheres.

Moreover, in the present embodiment, the numerical range of the surface electrical resistivity ρ is regulated. Therefore, it is easy to optimize the electrical characteristics of the conductive part 2. In other words, the PM sensor 1 of the present embodiment is such that electrodes 3a, 3b are formed on the major surface Si (refer to FIG. 2) of the conductive part 2, and when this PM sensor 1 is used, electrical current I flows near the surface of the conductive part 2. Consequently, electrical current I flows near the surface of the plate-shaped substrate 251 (refer to FIG. 18), and the measured surface electrical resistivity ρ can be said to be the electrical characteristic measured in a state that is close to the actual operating state of the PM sensor 1. Therefore, by regulating the numerical range of the surface electrical resistivity ρ, it is possible to regulate the electrical characteristics of the conductive part 2 in a state that is close to the actual operating state.

Furthermore, in the present embodiment, ceramic having a perovskite structure is used as the conductive material of the conductive part 2. When the molecular formula of this ceramic is set to be $ABO_3$, A is preferably at least one element selected from among La, Sr, Ca and Mg, and B is preferably at least one element selected from among Ti, Al, Zr and Y.

This kind of ceramic has high thermal resistance, and does not easily react chemically with substance that is included in exhaust gases. Therefore, this kind of ceramic can be suitably used as a conductive material for a PM sensor 1 that is exposed to exhaust gases.

Moreover, it is particularly preferred that the main component of A in the molecular formula described above is Sr and the accessory component is La, and that B is Ti.

As illustrated in FIG. 16, this kind of ceramic is such that change in the surface electrical resistivity ρ is small even when the temperature changes. This is considered to be due to the effect of adding La. By making the conductive part 2 using this kind of ceramic, it becomes possible to use an inexpensive measurement circuit as the measurement circuit for measuring the output of the PM sensor 1. In other words, as illustrated in FIG. 16, a ceramic ($SrTiO_3$) that does not include La is such that the surface electrical resistivity ρ greatly changes by approximately $1 \times 10^5$ to $1 \times 10^{11}$ Ω·cm cm in a temperature range of 100° C. to 500° C. Therefore, a conductive part 2 that is formed using this ceramic ($SrTiO_3$) is such that only a little electrical current flows near 100° C., and large electrical current flows near 500° C. Therefore, it is necessary to use an expensive measurement circuit having a large current measurement range. However, when a ceramic that includes La is used ($Sr_{1-x}La_xTiO_3$), it is possible to reduce the change in the surface electrical resistivity ρ in the temperature range 100° C. to 500° C. Therefore, it is possible to reduce the change in electrical current that flows in the conductive part 2 in this temperature range, and it becomes possible to use an inexpensive measurement circuit having a narrow electrical current measurement range.

The other configuration and effects are the same as in the first embodiment.

(Reference Embodiment 1)

The present embodiment is related to a PM sensor 1 that is able to increase detection sensitivity while at the same time providing a conductive part that covers a pair of electrodes 3a, 3b.

In the first embodiment, electrodes 3 were provided on the surface of a conductive part 2. As a result, electrical current flows in the surface of the conductive part 2, or in other words, electrical current flows in the accumulation surface 20. With this kind of configuration, even when only a small amount of PM accumulates on the accumulation surface 20, the current changes, so it is possible to increase the detection sensitivity for detecting PM.

However, in the present embodiment, by regulating the correlation between the thickness of the conductive part 2 and the thickness of the electrodes 3, it is possible to increase the detection sensitivity for detecting PM.

The main parts of the present embodiment will be explained using FIG. 22 to FIG. 25.

As in the first embodiment, the particulate matter detection apparatus 10 of the present embodiment includes a PM sensor 101, and a control unit 7 that is connected to that PM sensor 101. The control unit 7 has the same configuration as that of the first embodiment, so an explanation is omitted.

The PM sensor 101 of the present embodiment includes a substrate section 401 that is made using an insulating material, and plural electrode plate sections 402 on which electrodes are formed.

The substrate section 401 is made using the same material as the substrate section 4 in the first embodiment. Moreover, the electrode plate sections 402 have plate-shaped electrode substrate sections 412 made using an insulating material, detection-electrode sections 301, 302, and extending sections 303 that are electrically connected to the detection-electrode sections 301, 302. As will be described later, the detection-electrode sections 301, 302 are covered by a conductive part 200 (refer to FIG. 24).

The substrate section 401 and the electrode-plate sections 402 are formed in a rectangular plate shape. Moreover, the extending sections 303 are formed on the electrode substrate sections 412 so as to extend in the lengthwise direction. One end of the extending sections 303 is electrically connected to the control unit 7, and the other end is connected to the detection-electrode sections 301, 302.

Figure 22:
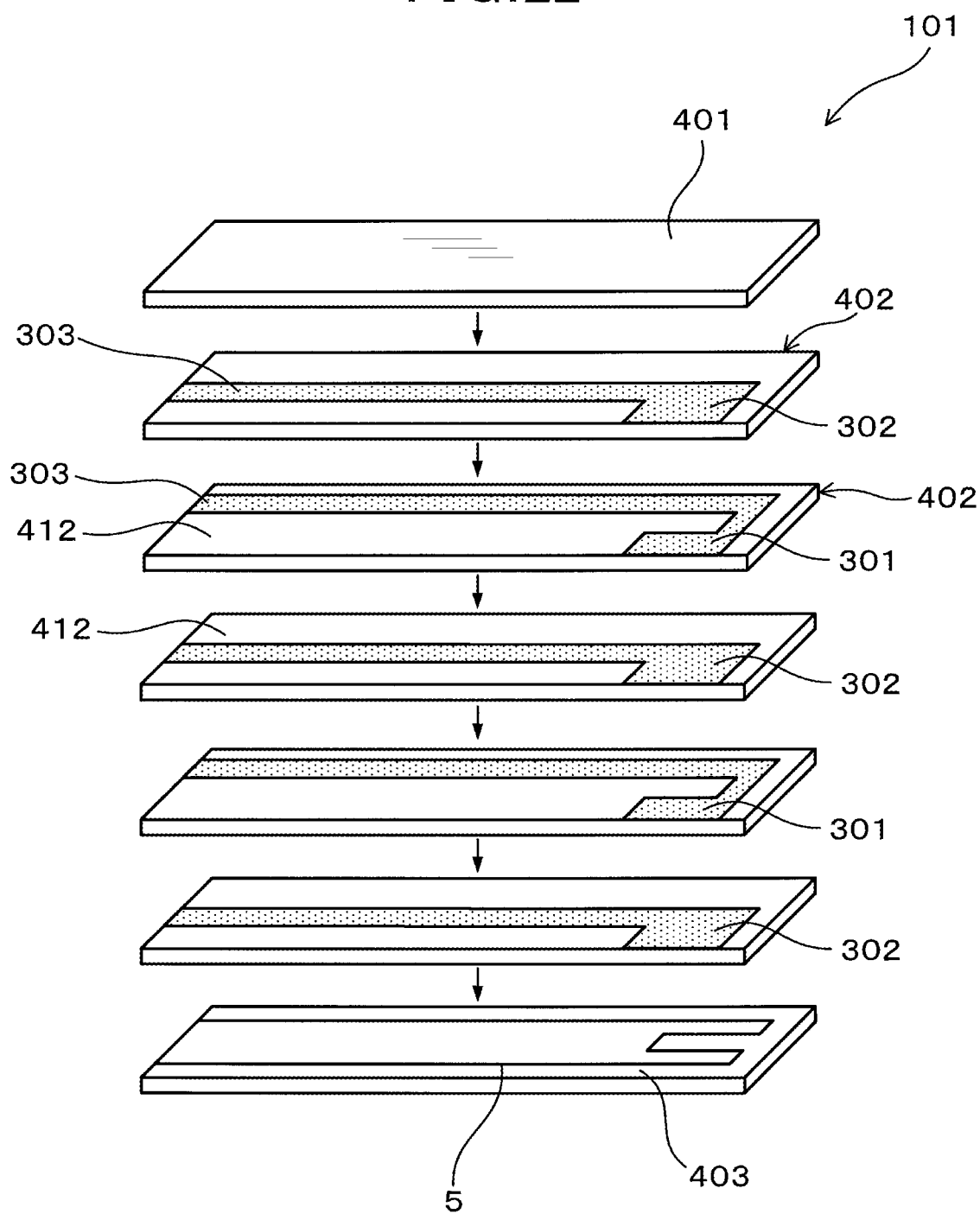
FIG. 22 is a perspective view of a disassembled particulate matter detection sensor in a first reference embodiment.

As illustrated in FIG. 22, the detection-electrode sections 301 that are positive electrodes and the detection-electrode sections 302 that are negative electrodes are alternately arranged. In this way, plural electrode plate sections 402 are layered so that adjacent electrodes have different polarity. Then, the substrate section 401 is arranged on one side in the layering direction of the electrode-plate sections 402, and a heater-plate section 403 having a heater 5 is arranged on the other side. The plural electrode-plate sections 402 are held in the layering direction by the substrate section 401 and the heater-plate section 403. As a result, a laminated body is formed.

Figure 23:
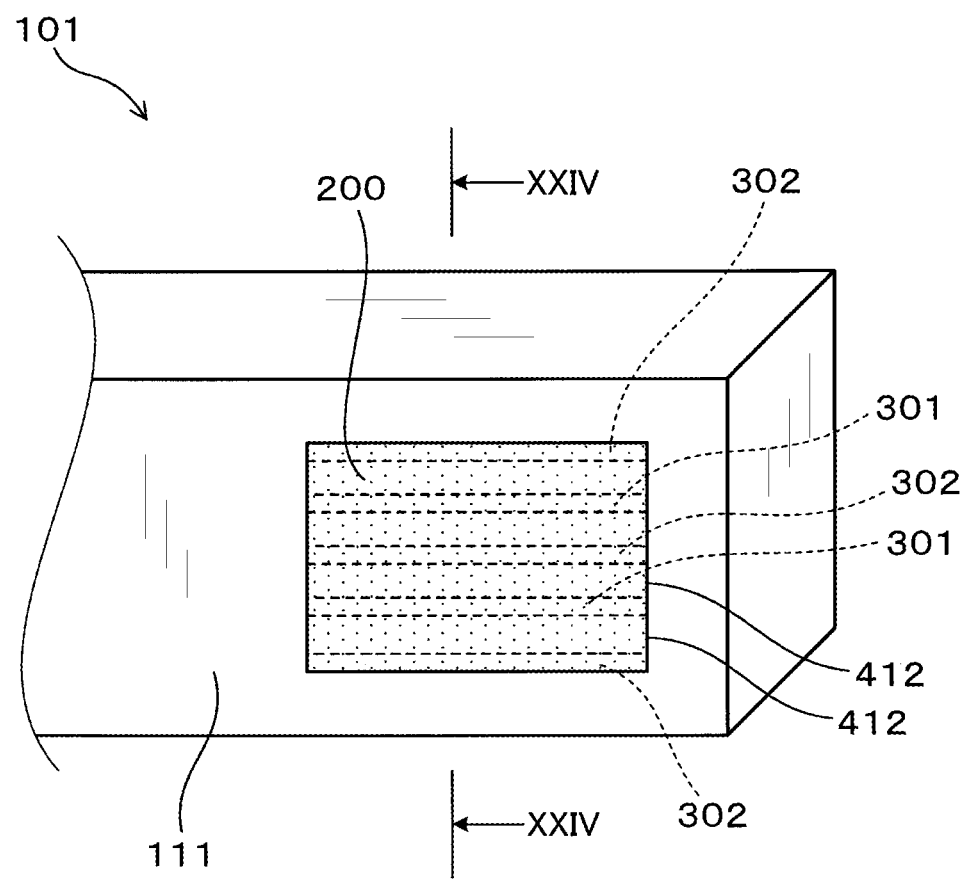
FIG. 23 is a perspective view of a particulate matter detection sensor in the first reference embodiment.
Figure 24:
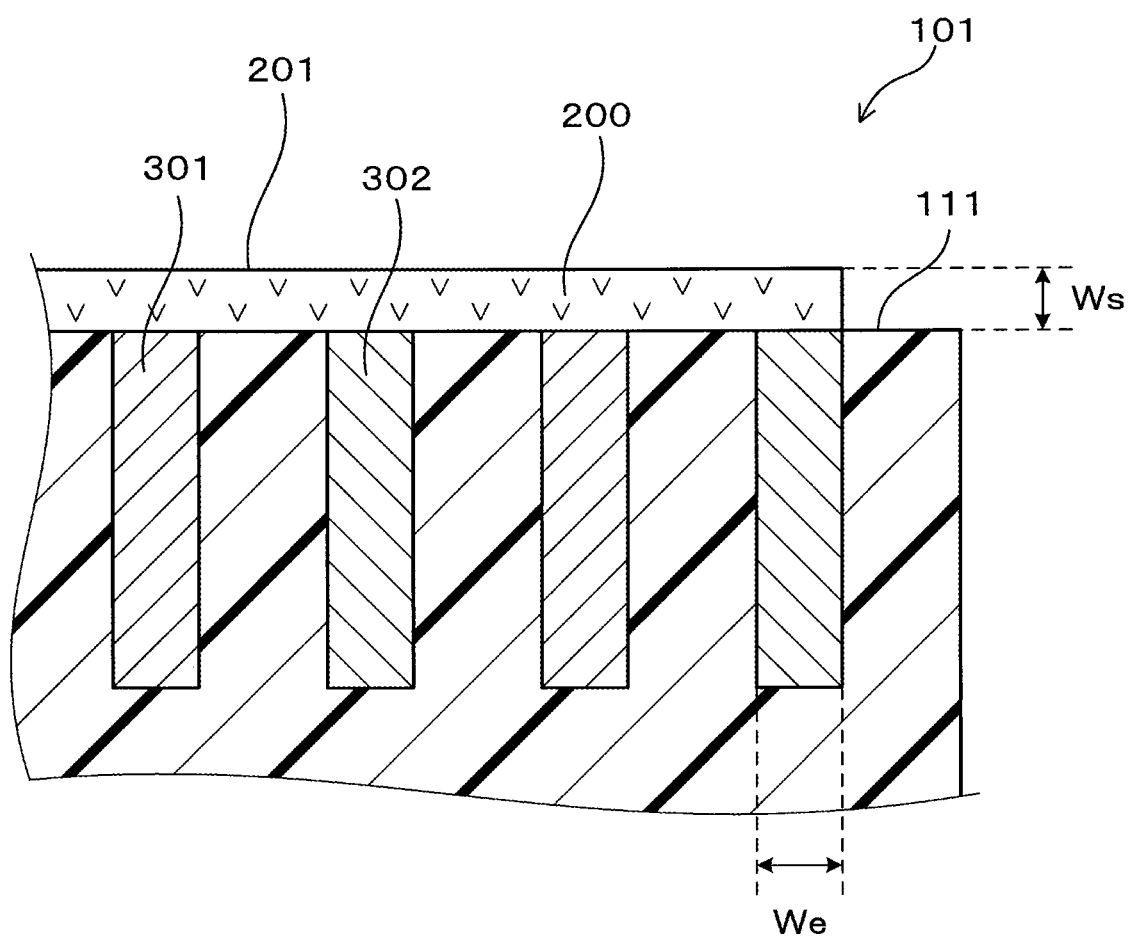
FIG. 24 is a cross-sectional view taken along a line XXIV-XXIV in FIG. 23.

As illustrated in FIG. 23, the detection-electrode sections 301, 302 and electrode-plate sections 412 are exposed from a part of the side surface 111 of the PM sensor 101. As illustrated in FIG. 24, the exposed detection-electrode sections 301, 302 and electrode-plate sections 412 are covered by the conductive part 200 having a specified thickness. The conductive part 200 can be formed using the same material as in the first embodiment.

Particulate matter accumulates on the accumulation surface 201 of the conductive part 200. The accumulation surface 201 is formed on the opposite side of the conductive part 200 from the side where the detection-electrode sections 301, 302 are arranged. The electrical resistivity of the conductive part 200 is higher than the electrical resistivity of the particulate matter, so electrical current flows more easily in the particulate matter than in the conductive part 200. Therefore, as in the first embodiment, when particulate matter accumulates on the accumulation surface 201, the electrical resistance between the detection-electrode sections 301, 302 decreases more than when particulate matter is not accumulated. Therefore, the measured value of the electrical current that is measured by the electrical current measurement unit 72 of the control unit 7 (refer to FIG. 8)

becomes larger. The calculation unit 73 calculates the amount of accumulated particulate matter using this measurement value.

As illustrated in FIG. 24, the thickness Ws of the conductive part 200 is formed so as to be less than the thickness We of the detection-electrode sections 301, 302.

By making the thickness Ws of the conductive part 200 less than the thickness We of the detection-electrode sections 301, 302 in this way, it is possible to improve the detection sensitivity for detecting particulate matter.

The effect of the present embodiment will be described in detail.

As illustrated in FIG. 22 and FIG. 24, electrode-substrate sections 412 made of an insulator are present between the pair of detection-electrode sections 301, 302. Therefore, electrical current does not flow to the electrode-substrate sections 412 even when voltage is applied to the pair of detection-electrode sections 301, 302. However, parts of the pair of electrodes 301, 302 are covered by the conductive part 200, so electrical current flows in this conductive part 200.

Figure 25:
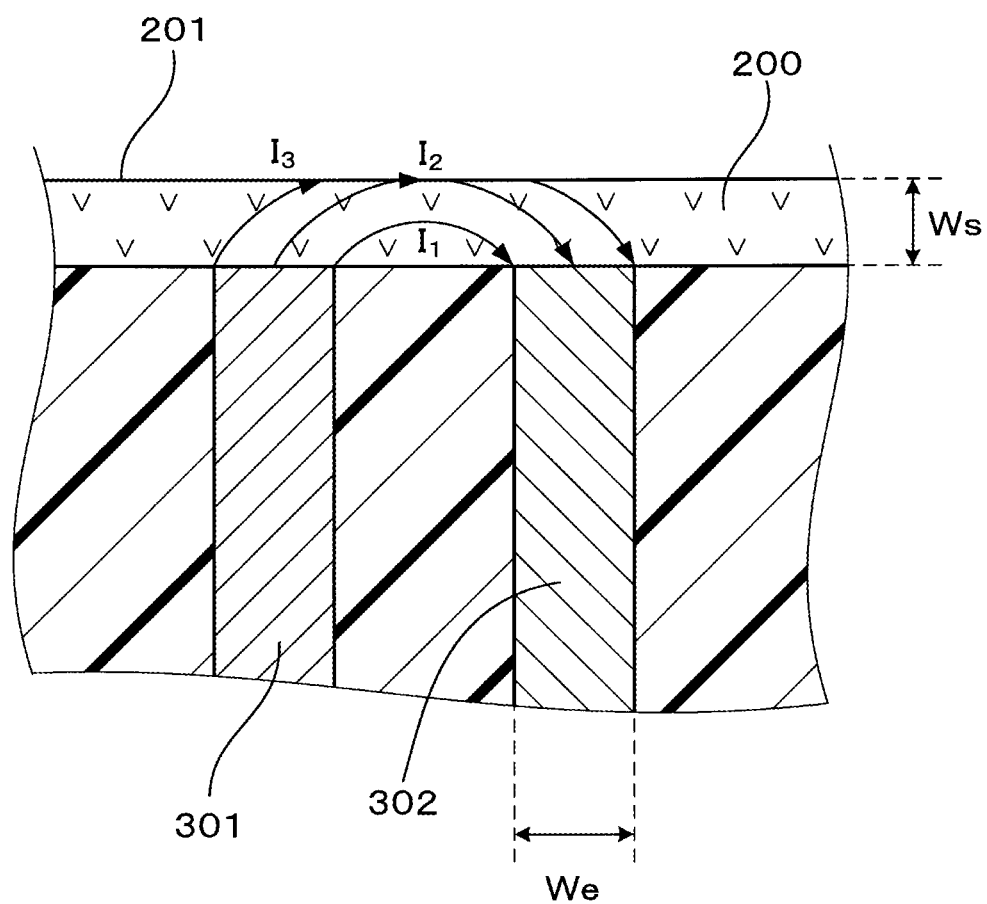
FIG. 25 is an enlarged view of a major part of FIG. 24.

As illustrated in FIG. 25, electrical current that flows from one of the detection-electrode sections 301 of the pair of detection-electrode sections 301, 302 curves inside the conductive part 200 and reaches the other detection-electrode section 302. Therefore, even when particulate matter is not adhered to the accumulation surface 201, a part of the electrical current is able to flow in the accumulation surface 201. When this happens, when the thickness Ws of the conductive part is thicker than the thickness We of the detection-electrode sections, the distance until the electrical current reaches the accumulation surface 201 becomes long, so the percentage of electrical current that flows inside the conductive part 200 becomes high, and the amount of electrical current that flows in the accumulation surface 201 decreases. Therefore, it becomes difficult to make the detection sensitivity for detecting PM high enough.

However, by making the thickness Ws of the conductive part 200 thinner than the thickness We of the detection-electrode sections as in the present embodiment, it is possible to reduce the amount of electrical current that is flowing inside the conductive part 200, and it is possible for much of the electrical current to flow in the accumulation surface 201. Therefore, when particulate matter adheres to the accumulation surface 201, it becomes easy for electrical current to flow in the particulate matter.

Therefore, even when only a small amount of particulate matter is accumulated on the conductive part 200, the rate of change of the current increases, and it is possible to improve the detection sensitivity for detecting particulate matter.

(Fifth Embodiment)

Figure 26:
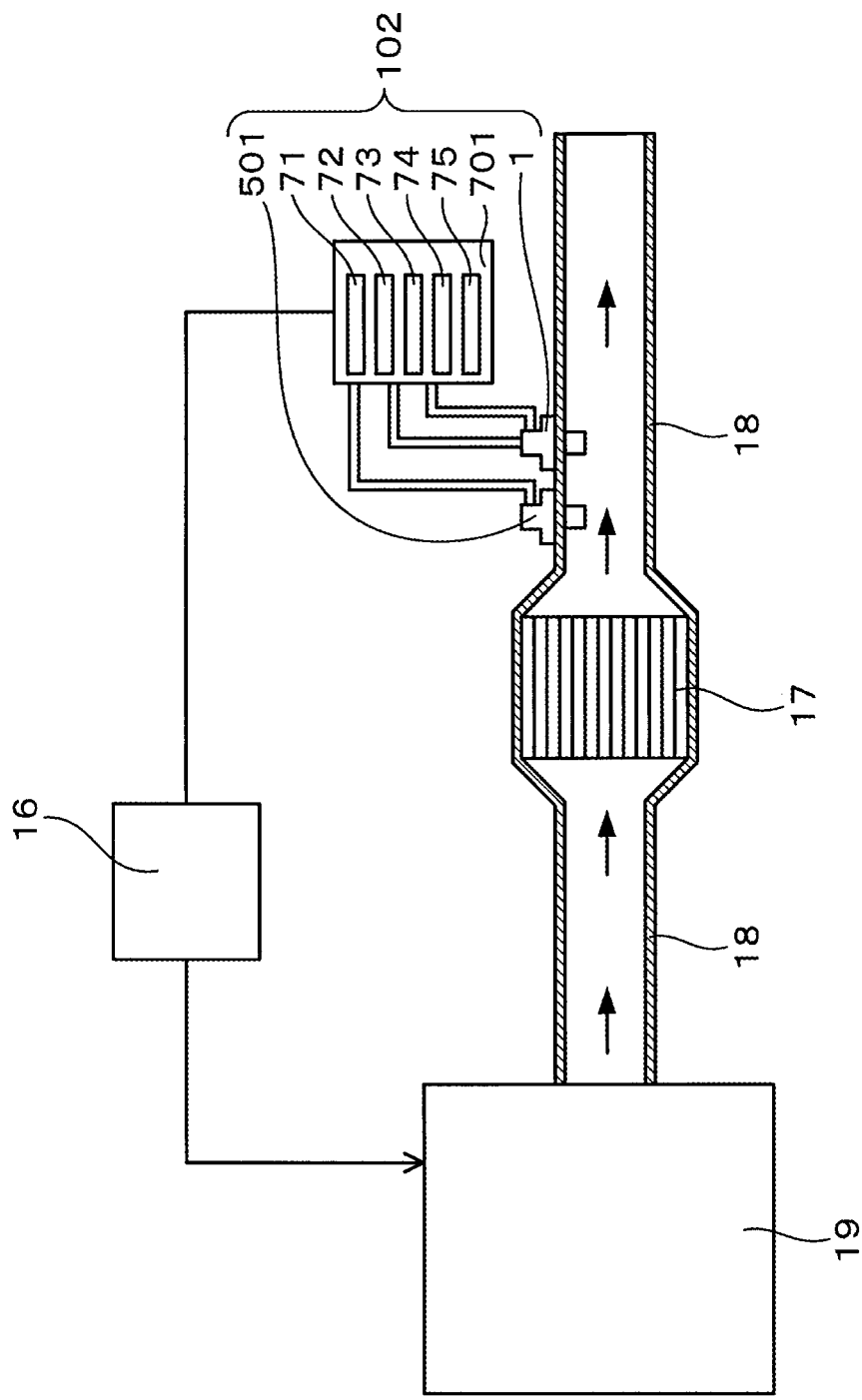
FIG. 26 is a conceptual diagram of a particulate matter detection apparatus in a fifth embodiment.

As illustrated in FIG. 26, the particulate matter detection apparatus 102 of the present embodiment includes a temperature-measurement unit 501 for detecting the temperature of exhaust gases. Moreover, in addition to the configuration of the first embodiment, the control unit 701 includes a resistance-correction unit 75 for correcting the resistance value of the conductive part 20 according the temperature of exhaust gases. In other words, the control unit 701 of the present embodiment includes a voltage-applying unit 71 that applies a voltage to the pair of electrodes, an electrical-current-measurement unit 72 that detects the electrical current of the current that flows between the pair of electrodes, a heater-control unit 74 that controls the heater 5, a calculation unit 73 that calculates the amount of accumulated particulate matter from the measurement value detected by the electrical-current-measurement unit 72, and calculates the amount of discharged particulate matter per unit time that is included in exhaust gases, and the resistance-correction unit 75 described above.

For the temperature-measurement unit 501 described above, a known exhaust-gases-temperature sensor can be used; for example, it is possible to use a temperature sensor that uses a thermistor as the thermosensitive element. The temperature-measurement unit 501 is provided near the PM sensor 1 that is installed in the exhaust pipe, and transmits detected temperature information to the resistance-correction unit 75 of the control unit 701. By providing the temperature-measurement unit 501 near the PM sensor 1, it is possible to use temperature measurements near the PM sensor 1 for correcting the resistance of the conductive part 2. Therefore it is possible to increase the accuracy for correcting the resistance.

It is not illustrated in the figures, however, the temperature information that is measured by the temperature-measurement unit 501 is also transmitted to the ECU 16 and used for injection control and the like of the engine.

In the present embodiment, the calculation unit 73 calculates the time derivative value, by taking the derivative over time of the measurement value from the electrical-current-measurement unit 72. This time derivative value is correlated with the amount of particulate matter in the exhaust gases. Moreover, the calculation unit 73 has quantity-correction data that corrects the amount of particulate matter per unit volume of exhaust gases. Using the time derivative value described above and the quantity-correction data, the calculation unit 73 is able to calculate the amount of particulate matter per unit volume of exhaust gases.

The resistance-correction unit 75 stores data (temperature characteristic data) for the relationship between the temperature and the electrical resistance of the conductive part 2. The resistance-correction unit 75 uses the temperature that is detected by the temperature-measurement unit 501 and the temperature characteristic data to calculate the correction resistance value for the conductive part 2. Then, using this correction resistance value, the resistance-correction unit 75 performs correction to reduce the effect of change due to temperature of the electrical resistance of the conductive part 2 that is included in the electrical resistance of the electrodes 3a, 3b.

As a result, it becomes possible to reduce the effect of the exhaust gases temperature on the conductive part 2 when detecting the amount of particulate matter. Therefore, it is possible to improve the detection accuracy for detecting particulate matter.

(Other Embodiments)

Embodiments of the present disclosure were described above, however, the present disclosure is not limited to the embodiments described above, and the disclosure can be applied to various embodiments within a range that does not depart from the scope of the disclosure, and particularly, it is possible to combine embodiments as long as trouble does not occur in doing so.

For example, it is presumed that the control unit 701 of the particulate matter detection apparatus 102 described in the fifth embodiment has a PM sensor 1 with the configuration of the first embodiment, however, it is also possible to employ the PM sensors of the second to fourth embodiments.

Moreover, in the reference embodiment 1, the conductive part 200 is provided on the side surface 111 of the PM sensor, however it may be provided on the end surface.

What is claimed is:

1. A particulate matter detection sensor for detecting an amount of particulate matter that is included in exhaust gases, comprising:
a conductive part that is formed into a plate shape using a conductive material having electrical resistivity that is higher than the particulate matter, with one major surface functioning as an accumulation surface on which the particulate matter accumulates; and
a pair of electrodes that are formed on the accumulation surface and arranged so as to be separated from each other and to face each other,
wherein the particulate matter detection sensor is configured to:
apply a first voltage between the electrodes without the particulate matter being accumulated on the accumulation surface to accordingly cause a first electrical current to flow through the accumulation surface such that the first electrical current is caused to flow through the accumulation surface even if no particulate matter is accumulated on the accumulation surface;
detect the first electrical current;
apply a second voltage between the electrodes with the particulate matter being accumulated on the accumulation surface to accordingly cause a second electrical current to flow through the accumulation surface and the particulate matter accumulated on the accumulation surface;
detect the second electrical current; and
detect the amount of the particulate matter based on an increase in the detected second electrical current relative to the detected first electrical current.

2. The particulate matter detection sensor according to claim 1, wherein
the electrodes include common sections and comb-tooth sections, with the comb-tooth sections that are formed on one electrode of the pair of electrodes and the comb-tooth sections that are formed on the other electrode alternately arranged, and a width of a comb-tooth section in an arrangement direction of the comb-tooth section is shorter than a space between pairs of comb-tooth sections.

3. The particulate matter detection sensor according to claim 1, wherein
the conductive material of the conductive part includes a metal oxide having conductivity.

4. The particulate matter detection sensor according to claim 1, wherein
a substrate section that is made of an insulating material is arranged on an opposite side of the conductive part from a side where the accumulation surface is formed; and
a heater for burning the particulate matter that accumulates on the accumulation surface is provided inside the substrate section.

5. The particulate matter detection sensor according to claim 1, wherein
a heater for burning the particulate matter that accumulates on the accumulation surface is provided inside the conductive part.

6. The particulate matter detection sensor according to claim 1, wherein
the conductive part is formed using the conductive material having a surface electrical resistivity $\rho$ determined such that samples are formed with a plate-shaped substrate made of the conductive material, having a thickness T of 1.4 mm, and the pair of electrodes formed on the major surface of the plate-shaped substrate, having length L and spacing D between electrodes,
an electrical resistance R between the pair of measurement electrodes is measured to calculate the surface electrical resistivity $\rho$ expressed by a following equation $$\rho = R \times L \times T/D$$

and the calculated surface electrical resistivity $\rho$ is between $1.0 \times 10^7$ to $1.0 \times 10^{10}$ $\Omega \cdot cm$ in a temperature range of 100° C. to 500° C.

7. The particulate matter detection sensor according to claim 1, wherein
the conductive material is a ceramic having perovskite structure and is expressed by the molecular formula $ABO3$, with A being at least one kind of element selected from among La, Sr, Ca and Mg, and B being at least one kind of element selected from among Ti, Al, Zr and Y.

8. The particulate matter detection sensor according to claim 7, wherein
a main component of A is Sr and an accessory component of A is La, and B is Ti.

9. The particulate matter detection sensor according to claim 1, wherein the first voltage is the same as the second voltage.

10. A particulate matter detection apparatus, comprising
the particulate matter detection sensor according to claim 1, and
a control unit that is electrically connected to the particulate matter detection sensor; wherein
the control unit includes:
a voltage-applying unit that applies a voltage between the pair of electrodes;
a electrical-current-measurement unit that measures electrical current that flows between the pair of electrodes; and
a calculation unit that calculates the amount of particulate matter that is included in exhaust gases based on the measurement value of the electrical current,
wherein the particulate matter detection sensor is configured to:
apply a first voltage between the electrodes without the particulate matter being accumulated on the accumulation surface to accordingly cause a first electrical current to flow through the accumulation surface such that the first electrical current is caused to flow through the accumulation surface even if no particulate matter is accumulated on the accumulation surface;
detect the first electrical current;
apply a second voltage between the electrodes with the particulate matter being accumulated on the accumulation surface to accordingly cause a second electrical current to flow through the accumulation surface and the particulate matter accumulated on the accumulation surface;
detect the second electrical current; and
detect the amount of the particulate matter based on an increase in the detected second electrical current relative to the detected first electrical current.

* * * * *